(12) United States Patent
Leitao

(10) Patent No.: US 9,290,446 B2
(45) Date of Patent: Mar. 22, 2016

(54) ELECTROPHILIC REAGENTS FOR MONOHALOMETHYLATION, THEIR PREPARATION AND THEIR USES

(75) Inventor: Emilia Perpetua Tavares Leitao, Sao Marcos (PT)

(73) Assignee: Hovione Inter Limited, Lucerne (CH)

( * ) Notice: Subject to any disclaimer, the term of this patent is extended or adjusted under 35 U.S.C. 154(b) by 154 days.

(21) Appl. No.: 13/882,127

(22) PCT Filed: Oct. 27, 2011

(86) PCT No.: PCT/GB2011/001541
§ 371 (c)(1),
(2), (4) Date: Jul. 5, 2013

(87) PCT Pub. No.: WO2012/056201
PCT Pub. Date: May 3, 2012

(65) Prior Publication Data
US 2013/0274460 A1    Oct. 17, 2013

(30) Foreign Application Priority Data

Oct. 27, 2010  (PT) .......................................... 105356
Oct. 18, 2011  (PT) .......................................... 105942

(51) Int. Cl.
| | | |
|---|---|---|
| C07C 317/00 | (2006.01) | |
| C07C 381/12 | (2006.01) | |
| C07J 3/00 | (2006.01) | |
| C07J 31/00 | (2006.01) | |

(52) U.S. Cl.
CPC ............. *C07C 381/12* (2013.01); *C07C 317/00* (2013.01); *C07J 3/005* (2013.01); *C07J 31/006* (2013.01)

(58) Field of Classification Search
USPC .......................................... 568/23, 53, 73, 74
See application file for complete search history.

(56) References Cited

U.S. PATENT DOCUMENTS

| | | | |
|---|---|---|---|
| 4,335,121 A | 6/1982 | Phillipps et al. | |
| 2002/0182185 A1 | 12/2002 | Wong | |
| 2011/0319637 A1 | 12/2011 | Shibata | |
| 2013/0225844 A1 | 8/2013 | Leitao | |

FOREIGN PATENT DOCUMENTS

| | | | |
|---|---|---|---|
| CH | 619968 A5 | 10/1980 | |
| CN | 1869039 A | 11/2006 | |
| CN | 100569784 C | 12/2009 | |
| DE | 2904614 A1 | 8/1979 | |
| EP | 1992612 A1 | 11/2008 | |
| GB | 1438940 | 6/1976 | |
| JP | 2010202539 A | 9/2010 | |
| PT | 105139 A | 12/2011 | |
| WO | 2007057152 A1 | 5/2007 | |
| WO | 2011151624 A1 | 12/2011 | |

OTHER PUBLICATIONS

Prakash; Organic Letters, 2008, vol. 10, No. 4, 557-560.*

Burton et al., "A Practical Synthesis of Fluoromethyltriphenylphosphonium Salts", Journal of Fluorine Chemistry, 1985, vol. 27, pp. 85-89.
Hu et al., "Selective difluoromethylation and monofluoromethylation reactions", Chem. Commun. 2009, pp. 7465-7478.

(Continued)

*Primary Examiner* — Fereydoun G Sajjadi
*Assistant Examiner* — Pancham Bakshi
(74) *Attorney, Agent, or Firm* — MacMillan, Sobanski & Todd, LLC

(57) ABSTRACT

The invention provides electrophilic monohalomethylating reagents, methods for their preparation and methods for preparation of monohalomethylated biologically active compounds using such reagents. Typical monohalomethyl groups transferred are FH2C—, ClH2C— and others. The reagents used for transferal of the groups are described by Formulae A-D: wherein: X=F, Cl, Br, I, sulfonate esters, phosphate esters or another leaving group; R11=tetrafluoroborates, inflates, halogen, perchlorate, sulfates, phosphates or carbonates The other variables are as defined in the claims.

Formula A

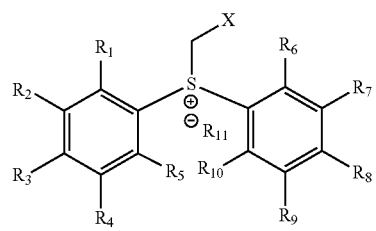

Formula B

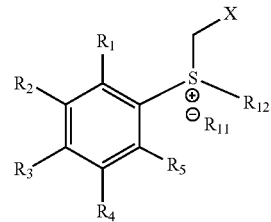

Formula C

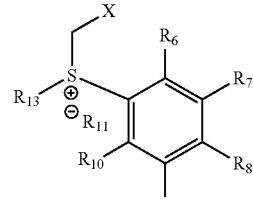

Formula D

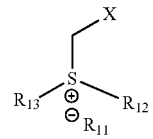

2 Claims, No Drawings

(56) References Cited

OTHER PUBLICATIONS

Pool, "The Elusive Replacements for CFCs", Science, 1989, vol. 242, pp. 666-668, Web accessed on Oct. 16, 2013, http://www.ciesin.org/docs/011-049/011-490.html.

Prakash et al., "Direct Electrophilic Monofluoromethylation", Organic Letters, 2008, vol. 10, No. 4, pp. 557-560.

Wenchao et al., "Manufacture and application of halogenated alkyl diphenylsulfonium hexafluorophosphate as cationic photo-initiator", Insight High Technology Co., Ltd., 2006.

Manteau et al. "New trends in the chemistry of α-fluorinated ethers, thioethers, amines and phosphines", Journal of Fluorine Chemistry, 2010, vol. 131, pp. 140-158.

* cited by examiner

ELECTROPHILIC REAGENTS FOR MONOHALOMETHYLATION, THEIR PREPARATION AND THEIR USES

This is a national stage application filed under 37 CFR §1.371 of international application PCT/GB2011/001541 filed Oct. 27, 2011, which claims priority to Ser. PT/105356 filed Oct. 27, 2010, the entire disclosures of which are expressly incorporated herein by reference.

The present invention provides electrophilic monohalomethylating reagents, methods for their preparation and methods for preparation of monohalomethylated biologically active compounds using such reagents.

The monofluoromethyl group ($CH_2F$) is an important structural moiety in various classes of bioactive organic molecules. The investigation of di- and monofluoromethylated compounds as organic biologically active compounds has emerged recently. As a result, a variety of structurally diverse —$CH_2F$ containing drugs have been developed, such as: afloqualone, fluticasone Propionate (Jinbo Hu; Wei Zhang; Fei Wang; *Chem. Commum.*, 2009, 7465-7478), the anaesthetic sevoflurane and fluticasone furoate. The efficient and selective incorporation of monofluoromethylated moieties into the organic molecule is usually carried out directly using $CH_2FBr$ or indirectly, using reagents such as $CH_2BrI$ or $CH_2ClI$, amongst others. These compounds are known as halons or freons (HCFCs), which is a subclass of chlorofluorocarbons (CFCs).

The use of this class of compounds includes refrigerants, blowing agents, propellants in medicinal applications and degreasing solvents (M. Rossberg et al. "Chlorinated Hydrocarbons" in Ullmann's Encyclopedia of Industrial Chemistry 2006, Wiley-VCH, Weinheim).

Unfortunately, due to their high stability, they do not decompose in the lower atmosphere as many industrial chemicals do. In fact they are accumulating and eventually rise to the stratosphere. Ultraviolet radiation in the stratosphere breaks the CFCs apart, and the released chlorine or bromine atoms destroy the ozone layer. For this reason, the manufacture of such compounds is being phased out according to the Montreal Protocol (Pool, R. 1989. Replacements for CFCs have proven elusive. *Science* 242: 666). Under the Montreal Protocol it was agreed to start reducing the consumption and production of ozone depleting chemicals in 2015. Therefore, there is a need for alternative reagents to carry out the monofluoromethylations, instead of using reagents that deplete the ozone layer.

Recently, Prakash et al. reported a new electrophilic monofluoromethylation reagent for direct transfer of $^+CH_2F$ (S-monofluoromethyl-5-phenyl-2,3,4,5-tetramethylphenyl-sulfonium triflate and tetrafluoroborate) (G. K. Surya Prakash; Istvan Ledneczki; Sujith Chacko; George A. Olah; *Org. Lett.*, vol. 10, No. 4, 2008), this reagent is expensive mainly due to the cost of the substituent 1,2,3,4-tetramethylbenzene.

These reagents (S-monofluoromethyl-S-phenyl-2,3,4,5-tetramethylphenylsulfonium tetrafluoroborate and triflate) were successfully tested in the preparation of biologically active compounds containing a "$CH_2F$" moiety as reported in our co-pending Patent application PT105139.

According to the present invention, we have now found that surprisingly the same reagents can be prepared with other substituted methyl groups —$CH_2X$. Especially important are reagents in which X is a "good leaving group", such as: fluorine, chorine, bromine, iodine, sulfonate esters, phosphate esters, etc. By "leaving group" we mean a molecular fragment that departs with a pair of electrons. We prefer to use a good leaving group, for example one which is a weak base as will be clear to those in the art. Good leaving groups generally have a low pKa. Thus, a pKa of ≤2, or a pKa≤0, is preferred. A pKa of from −1 to −10 or lower is generally suitable. "Good leaving groups" are, for example, the conjugated base of a strong acid, and are weak bases.

These reagents can be used to incorporate efficiently and selectively $CH_2X$ moieties such as $CH_2F$, $CH_2Cl$, $CH_2Br$, $CH_2I$ amongst others into organic biologically active compounds or into intermediates in the synthesis of the organic biologically active compounds. In the case where intermediates are produced in the reaction the final product is produced by the transformation of the incorporated group —$CH_2X$ of the intermediate into the desired halomethyl group.

This invention aims at solving the problem of offering alternative reagents to incorporate the —$CH_2X$ moiety into substrates. We have found this can be achieved, for example, by the preparation and use of reagents of formulas presented in Table 1.

According to one aspect of the present invention, there is provided a compound of formula A, B, C or D

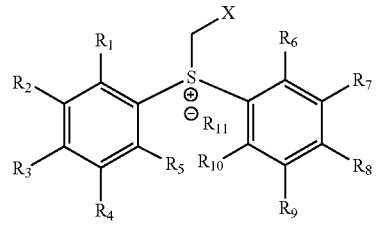

Formula A

Wherein:
X=F, Cl, Br, I, sulfonate esters, phosphate esters or another leaving group
R1, R2, R3, R4, R5, R6, R7, R8, R9, R10 are each individually selected from H, alkyl, aryl, alkynyl, alkenyl, cycloalkyl, cycloalkenyl, alkoxy, nitro, halogen or amino; preferably selected from H, $C_1$-$C_{10}$ alkyl, aryl, $C_1$-$C_{10}$ alkynyl, $C_1$-$C_{10}$ alkenyl, $C_1$-$C_{10}$ cycloalkyl, $C_1$-$C_{10}$ cycloalkenyl, $C_1$-$C_{10}$ alkoxy, nitro, halogen or amino
R11=tetrafluoroborate, triflate, halogen, perclorate, sulfates, phosphates or carbonates
Excluding the case when: X=F and R1=R2=R3=R4=R5=H and R6=R7=R8=R9=methyl, R10=H and R11=triflate or tetrafluoroborate; or

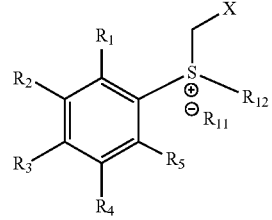

Formula B

Wherein:
X=F, Cl, Br, I, sulfonate esters, phosphate esters or another leaving group; and
R1, R2, R3, R4, R5 are each individually selected from H, alkyl, aryl, alkynyl, alkenyl, cycloalkyl, cycloalkenyl, alkoxy, nitro, halogen or amino; preferably selected from H, $C_1$-$C_{10}$ alkyl, aryl, $C_1$-$C_{10}$ alkynyl, $C_1$-$C_{10}$ alkenyl, $C_1$-$C_{10}$ cycloalkyl, $C_1$-$C_{10}$ cycloalkenyl, alkoxy, nitro, halogen or amino
and
R11=tetrafluoroborate, triflate, halogen, perchlorate, sulfates, phosphates or carbonates; and
R12=resin, naphthalene or substituted naphthalene
Excluding the case when: X=F and R1=R2=R3=R4=R5=H and R6=R7=R8=R9=methyl, R10=H and R11=triflate or tetrafluoroborate and when X=F and R1=R2=R3=R4=R5=H and R12=poly(styrene-co-divinylbenzene) and R11=triflate or tetrafluoroborate; or

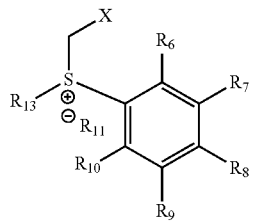

Formula C

Wherein:
X=F, Cl, Br, I, sulfonate esters, phosphate esters or another leaving group
R13=naphthalene or substituted naphthalene
R6, R7, R8, R9, R10 are each individually selected from H, alkyl, aryl, alkynyl, alkenyl, cycloalkyl, cycloalkenyl, alkoxy, nitro, halogen or amino; preferably selected from H, $C_1$-$C_{10}$ alkyl, aryl, $C_1$-$C_{10}$ alkynyl, $C_1$-$C_{10}$ alkenyl, $C_1$-$C_{10}$ cycloalkyl, $C_1$-$C_{10}$ cycloalkenyl, $C_1$-$C_{10}$ alkoxy, nitro, halogen or amino
R11=tetrafluoroborate, triflate, halogen, perchlorate, sulfates, phosphates or carbonates; or

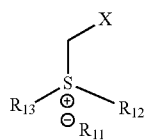

Formula D

X=F, Cl, Br, I, sulfonate esters, phosphate esters or another leaving group
R13=naphthalene or substituted naphthalene
R11=tetrafluoroborate, triflate, halogen, perchlorate, sulfates, phosphates or carbonates
R12=resin, naphthalene or substituted naphthalene.

In another aspect, the present invention provides a process for making an organic biologically active compound containing a "$CH_2X$" moiety, or an intermediate therefor, which process comprises the step of monohalomethylation, wherein the monohalomethylating reagent used is a compound of formula A, B, C or D as defined herein.

The step of monohalomethylation may, for example, comprise reacting an intermediate compound for the said organic biologically active compound with a monohalomethylating reagent according to invention. The resulting compound may be the biologically active compound of interest, or a further intermediate which may then be converted into the biologically active compound of interest.

In a further aspect, the invention provides a process for making a compound of formula A, B, C, or D, wherein the process comprises the step of preparing a compound of formula E or F:

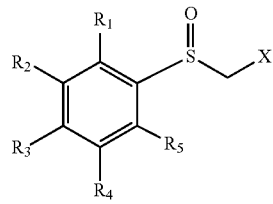

Formula E

Wherein:
R1, R2, R3, R4, R5 are each individually selected from H, alkyl, aryl, alkynyl, alkenyl, cycloalkyl, cycloalkenyl, alkoxy, nitro, halogen or amino; preferably selected from H, $C_1$-$C_{10}$ alkyl, aryl, $C_1$-$C_{10}$ alkynyl, $C_1$-$C_{10}$ alkenyl, $C_1$-$C_{10}$ cycloalkyl, cycloalkenyl, $C_1$-$C_{10}$ alkoxy, nitro, halogen or amino
X=F, Cl, Br, I, sulfonate esters, phosphate esters or another leaving group

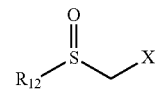

Formula F

Wherein:
R12=resin, naphthalene or substituted naphthalene
X=F, Cl, Br, I, sulfonate esters, phosphate esters or another leaving group; and converting the compound into a compound of formula A, B, C or D.

In a further aspect, the invention provides the use of a compound according to the invention as defined herein to manufacture an organic biologically active compound containing a "$CH_2X$" moiety.

TABLE 1

| Monohalomethylating reagents | |
|---|---|
| Formula | Substituent |
| (structure shown) | X = F, Cl, Br, I, sulfonate esters, phosphate esters or other leaving groups, preferably good leaving groups<br>R1, R2, R3, R4, R5, R6, R7, R8, R9, R10 = H, alkyl, aryl, alkynyl, alkenyl, cycloalkyl, cycloalkenyl, alkoxy, nitro, halogen or amino; preferably selected from H, $C_1$-$C_{10}$ alkyl, aryl, $C_1$-$C_{10}$ alkynyl, $C_1$-$C_{10}$ alkenyl, $C_1$-$C_{10}$ cycloalkyl, $C_1$-$C_{10}$ cycloalkenyl, $C_1$-$C_{10}$ alkoxy, nitro, halogen or amino<br>R11 = tetrafluoroborate, triflate, halogen, perchlorate, sulfates, phosphates or carbonates<br>Excluding the case when: X = F and R1 = R2 = R3 = R4 = R5 = H and R6 = R7 = R8 = R9 = methyl, R10 = H and R11 = triflate or tetrafluoroborate |

TABLE 1-continued

Monohalomethylating reagents

| Formula | Substituent |
|---|---|
| (structure: benzene ring with $R_1$-$R_5$ substituents and $-S^+(R_{11})(R_{12})-CH_2X$ group) | X = F, Cl, Br, I, sulfonate esters, phosphate esters or other leaving groups, preferably good leaving groups<br>R1, R2, R3, R4, R5 = H, alkyl, aryl, alkynyl, alkenyl, cycloalkyl, cycloalkenyl, alcoxy, nitro, halogen or amino; preferably selected from H, $C_1$-$C_{10}$ alkyl, aryl, $C_1$-$C_{10}$ alkynyl, $C_1$-$C_{10}$ alkenyl, $C_1$-$C_{10}$ cycloalkyl, $C_1$-$C_{10}$ cycloalkenyl, $C_1$-$C_{10}$ alkoxy, nitro, halogen or amino<br>R11 = tetrafluoroborate, triflate, halogen, perclorate, sulfates, phosphates or carbonates<br>R12 = resin, naphthalene or substituted naphthalene<br>Excluding the case when: X = F and R1 = R2 = R3 = R4 = R5 = H and R6 = R7 = R8 = R9 = methyl, R10 = H and R11 = triflate or tetrafluoroborate and when X = F and R1 = R2 = R3 = R4 = R5 = H and R12 = poly(styrene-co-divinylbenzene) and R11 = triflate or tetrafluoroborate |
| (structure: benzene ring with $R_6$-$R_{10}$ substituents and $-S^+(R_{11})(R_{13})-CH_2X$ group) | X = F, Cl, Br, I, sulfonate esters, phosphate esters or other leaving groups, preferably good leaving groups<br>R13 = naphthalene or substituted naphthalene<br>R6, R7, R8, R9, R10 = H, alkyl, aryl, alkynyl, alkenyl, cycloalkyl, cycloalkenyl, alcoxy, nitro, halogen or amino; preferably selected from H, $C_1$-$C_{10}$ alkyl, aryl, $C_1$-$C_{10}$ alkynyl, $C_1$-$C_{10}$ alkenyl, $C_1$-$C_{10}$ cycloalkyl, $C_1$-$C_{10}$ cycloalkenyl, $C_1$-$C_{10}$ alkoxy, nitro, halogen or amino R11 = tetrafluoroborate, triflate, halogen, perclorate, sulfates, phosphates or carbonates |
| (structure: $R_{13}$-$S^+(R_{11})(R_{12})$-$CH_2X$) | X = F, Cl, Br, I, sulfonate esters, phosphate esters or other leaving groups, preferably good leaving groups<br>R13 = naphthalene or substituted naphthalene<br>R11 = tetrafluoroborate, triflate, halogen, perclorate, sulfates, phosphates or carbonates<br>R12 = resin, naphthalene or substituted naphthalene |

These reagents can be used successfully in the preparation of monohalomethylated organic biologically active compounds containing the $CH_2X$ moiety, such as fluticasone propionate, fluticasone furoate, loteprednol etabonate and intermediates for such compounds and others as described in patents U.S. Pat. No. 4,335,121, WO2007/57152, US2002/182185, DE2904614, CH619968.

This invention provides monohalomethylating reagents, methods for their preparation, and methods for preparation of monohalomethylated organic biologically active compounds using these reagents.

One aspect of this invention concerns monohalomethylating reagents of the formulas described in Table 1 and their preparation.

The monohalomethylating reagents of this invention, according to the formulas in Table 1, may, for example, be prepared in a one pot reaction, isolating each intermediate or combining reactions and isolating intermediates.

The reactions can be carried out starting from an organic compound, such as the ones described in Table 2.

TABLE 2 starting materials

| Formula | Substituent |
|---|---|
| (benzene ring with $R_1$-$R_5$ and $-S-CH_3$) | R1, R2, R3, R4, R5 = H, alkyl, aryl, alkynyl, alkenyl, cycloalkyl, cycloalkenyl, alkoxy, nitro, halogen or amino; preferably selected from H, $C_1$-$C_{10}$ alkyl, aryl, $C_1$-$C_{10}$ alkynyl, $C_1$-$C_{10}$ alkenyl, $C_1$-$C_{10}$ cycloalkyl, $C_1$-$C_{10}$ cycloalkenyl, $C_1$-$C_{10}$ alkoxy, nitro, halogen or amino |
| (benzene ring with $R_1$-$R_5$ and $-S(=O)-CH_3$) | |
| $R_{12}-S-CH_3$ | R12 = resin, naphthalene or substituted naphthalene |
| $R_{12}-S(=O)-CH_3$ | |

These compounds can be used to prepare the intermediates of Table 3.

TABLE 3 intermediates

| Formula | Substituent |
|---|---|
| (benzene ring with $R_1$-$R_5$ and $-S(=O)-CH_2X$) | R1, R2, R3, R4, R5 = H, alkyl, aryl, alkynyl, alkenyl, cycloalkyl, cycloalkenyl, alcoxy, nitro, halogen or amino; preferably selected from H, $C_1$-$C_{10}$ alkyl, aryl, $C_1$-$C_{10}$ alkynyl, $C_1$-$C_{10}$ alkenyl, $C_1$-$C_{10}$ cycloalkyl, $C_1$-$C_{10}$ cycloalkenyl, $C_1$-$C_{10}$ alkoxy, nitro, halogen or amino<br>X = F, Cl, Br, I, sulfonate esters, phosphate esters or other leaving groups, preferably good leaving groups |
| $R_{12}-S(=O)-CH_2X$ | R12 = resin, naphthalene or substituted naphthalene<br>X = F, Cl, Br, I, sulfonate esters, phosphate esters or other leaving groups, preferably good leaving groups |

The reactions can be carried within a suitable temperature range and in the presence of an organic solvent and an organic or inorganic catalyst. The reactions can be carried out in the presence of other chemical compounds such as: oxidizing agents, reductive agents, organic or inorganic bases, halogenating agent. The reagents can also be prepared as salts.

The monohalomethylating reagents obtained, can be isolated and purified by any conventional method. Examples of such methods include but are not limited to: direct crystallization from the reaction mixture; by addition of an anti-solvent at a controlled pH; by addition of water of a controlled pH; by extraction with an organic solvent and washing with an appropriate non-miscible phase; by re-crystallization in organic solvent or by column chromatography. Resins and activated charcoal can also be used during the work-up to purify the monohalomethylating reagent.

The reagents can be used either as described above or bound to a solid phase. When the reagents are bound to a resin this facilitates the removal of by-products from the reaction mixture.

A further aspect of this invention concerns methods for preparation of monohalomethylated organic biologically active compounds using the monohalomethylating reagents described above.

The monohalomethylated organic biologically active compounds can be prepared by reaction of the monohalomethylating reagents with a substrate. For example, the substrate may be an intermediate compound which is a precursor compound, including a direct precursor compound, to the organic biological compound of interest. Such precursor compounds will be clear to those in the art.

The reactions can be carried within a suitable temperature range and in the presence of an organic solvent and an organic or inorganic catalyst. The reactions can be carried out in the presence of other chemical compounds such as: oxidizing agents, reductive agents, organic or inorganic bases, halogenating agent.

The monohalomethylated organic biologically active compounds obtained can be isolated and purified by any conventional method. Examples of such methods include, but are not limited to: crystallization from the reaction mixture; addition of an anti-solvent to the reaction mixture; addition of water at a controlled pH. The organic biologically active compounds can also be isolated by extraction with an organic solvent and/or concentration wherein the organic layers can be washed with a suitable non-miscible solvent at a defined pH and may contain reductive agents. After or during the washes the organic layers can be dried with drying agents. Resin and activated charcoal can also be used during the work-up to purify the organic extracts. The monohalomethylated organic biologically active compounds isolated from the reactions as described above can be purified by any conventional methods examples of such methods include but are not limited to: re-crystallization or column chromatography.

The monohalomethylated organic biologically active compounds obtained can be used as pharmaceutical active ingredients formulated as known and used in the treatment of several medical conditions.

The following examples are given as illustrative and by no means should be considered as limiting the scope of the invention.

EXAMPLE 1

One-pot Synthesis of monofluoromethyl phenyl sulfoxide Starting from methylphenylsulfoxide (Compound II)

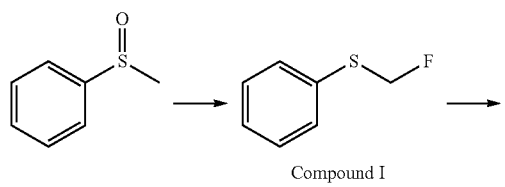

Compound I

-continued

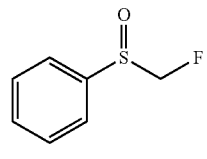

Compound II

Methylphenylsulfoxide (65 g, 463.61 mmol) was dissolved in dichloromethane (500 mL) under an nitrogen atmosphere. The solution was cooled to a temperature below −5° C. DAST (100 mL, 1.65 eq) was added slowly maintaining the same temperature. The reaction mixture was warmed up to room temperature and stirred for 1 hour at this temperature and then, overnight at the same temperature. Water (300 mL) was added after cooling the mixture to 0° C. and then the reaction mixture was warmed up until a temperature between 20° C. and 25° C. The resulting mixture was stirred and the layers were separated. The aqueous phase was extracted with DCM (3×400 mL). The combined organic phase was washed with saturated NaHCO$_3$ (400 mL) and saturated NaCl solution (400 mL) and then was concentrated to dryness, an oily residue was obtained. The residue was cooled to 0° C. and dissolved in a mixture of methanol (297.1 mL) and water (59.4 mL). NBS (N-bromo Succinimide (100.5 g, 1.5 eq) was added in small portions and the resulting solution was stirred at the same temperature until the reaction was complete. The mixture was quenched with the addition of Na$_2$SO$_3$ solution (10%, 300 mL). Saturated NaHCO$_3$ solution was added to adjust the pH between 7 and 8 and then the mixture was concentrated under vacuum at a temperature between 30° C. and 35° C. The residue was extracted with dichloromethane (3×300 mL). The combined organic phase was dried with anhydrous sodium sulfate and then concentrated under vacuum to give the crude product as yellow oil, 58 g.

EXAMPLE 2

Preparation of monofluoromethyl phenyl sulfoxide, Starting from methylphenylsulfide, Isolating Each Intermediate

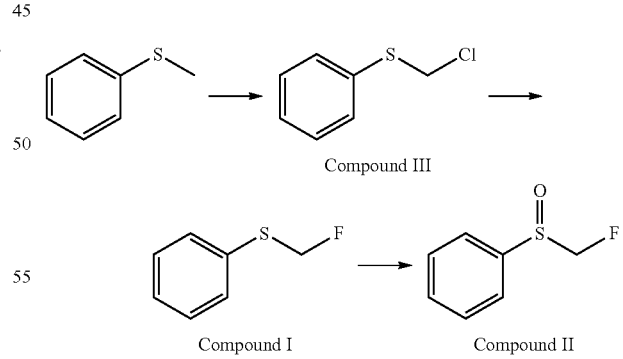

Compound III

Compound I          Compound II

1) Preparation of chloromethyl phenyl (Compound III)

Methylphenylsulfide (100 g, 805.13 mmol) was diluted in chorobenzene (602 mL). N-Chloro Succinimide (NCS) (112.89 g, 1.05 eq) was added in small portions maintaining the temperature between 35° C. and 45° C., under an argon atmosphere. After 3 hours, the suspension formed was filtered, and the solid was washed with chlorobenzene (50 mL). The filtrate was washed with water (3×300 mL). The resulting organic phase was dried with magnesium sulfate and concentrated. The crude product was purified by distillation to give 98 g (77%) of the desired product as yellow oil (bp: 62° C. at 40 Pa).

2) Preparation of fluoromethyl phenyl sulphide (Compound I)

Cesium fluoride (191.50 g, 2 eq) was added to a mixture of PEG400 (100 mL) and acetonitrile (600 mL). The mixture was stirred for a few minutes under an argon atmosphere and then acetonitrile (100 mL) was removed by distillation. Chloromethyl phenyl sulfide (100 g, 630.32 mmol) was added and the resulting mixture was stirred for 6 hours at a temperature between 80° C. and 85° C. The mixture was filtered and the filtrate was concentrated. The crude product was purified by distillation to give 52.46 g (58.5%) of the desired product as slightly yellow oil (bp: 43° C. at 40 Pa).

3) Preparation of monofluoromethyl phenyl sulfoxide (Compound II)

Fluoromethyl phenyl sulphide (85 g, 351.63 mmol) was added to a mixture of methanol (250 ml) and water (50 mL). The resulting mixture was cooled to a temperature between 0° C. and 5° C. NBS (75.10 g, 1.2 eq) was added in small portions maintaining the same temperature range. The reaction mixture was stirred until the reaction was complete, and then, was quenched with $Na_2SO_3$ solution (10%, 150 mL). The pH of the reaction mixture was adjusted to a value between 7 and 8 with $NaHCO_3$ saturated solution. The mixture was concentrated under vacuum at a temperature between 20° C. and 25° C. The residue was extracted with dichloromethane (200 mL, 300 mL). The combined organic layer was washed with water (2×300 mL) and concentrated to ⅓ of the volume. Heptane (50 mL) was added and the resulting mixture was concentrated again. The crude product was purified by flash chromatography (Ethyl Acetate/Hexane 30:70) to give 49.8 g (89.6%) of the desired product as colourless oil at rt, which is a white solid at −20° C.

EXAMPLE 3

Preparation of (3,4-dimethylphenyl)(fluoromethyl)(phenyl)sulfonium tetrafluoroborate

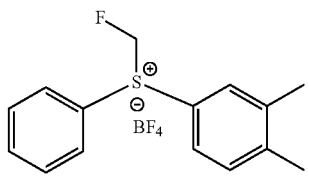

Monofluoromethyl phenyl sulfoxide (645 mg, 4.08 mmol) of example 2 was dissolved in dry diethyl ether (15 ml) under argon atmosphere. O-xylene (0.54 ml, 1.1 eq) was added to the previous solution and then the mixture was cooled to a temperature below −50° C. After stabilizing the temperature, trifluoromethanesulfonic anhydride (0.68 mL, 1.0 eq) was added slowly maintaining the same temperature. The mixture was stirred until the reaction was complete. $HBF_4$ solution (54%, 1.12 mL, 2 eq) was added and the resulting suspension was stirred for 30 minutes. The precipitate tetrafluoroborate salt was isolated by filtration, washed with diethyl ether at 0° C. and dried. The desired product was obtained as a slightly yellow oily solid (1.729 g).

$^1$H NMR (CDCl$_3$, 400 MHz): δ 7.83 (2H, d, J=7.8 Hz), 7.76-7.56 (5H, m), 7.43 (1H, d, J=8.1 Hz), 6.54 (2H, ddd, J=46.4, J=26.9, J=9.3 Hz), 2.37 (3H, s), 2.36 (3H, s). $^{13}$C NMR (CDCl$_3$, 100 MHz): δ 145.6, 141.1, 138.8, 134.6, 132.5, 132.2, 132.1, 131.3, 131.07, 131.06, 129.6, 129.06, 129.04, 90.6 (d, J=241.9 Hz), 20.1, 19.9. FT-IR (film): 3018, 2956, 1448, 1259, 1162, 1058, 1029 cm$^{-1}$.

EXAMPLE 4

Preparation of (2,5-dimethylphenyl)(fluoromethyl)(phenyl)sulfonium tetrafluoroborate

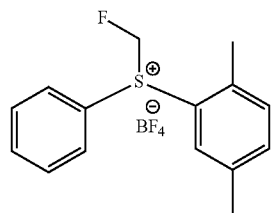

Monofluoromethyl phenyl sulfoxide (1.01 g, 6.38 mmol) of example 2 was dissolved in dry diethyl ether (15 mL) under an argon atmosphere. p-Xylene (0.87 mL, 1.1 eq) was added to the previous solution and then the mixture was cooled to a temperature below −50° C. After stabilizing the temperature, trifluoromethanesulfonic anhydride (1.07 mL, 1.0 eq) was added slowly, maintaining the same temperature. The mixture was stirred, at the same temperature, until the reaction was complete. $HBF_4$ in $Et_2O$ solution (54%, 1.76 mL, 2 eq) was added and then resulting mixture was stirred for 30 minutes. The solid was isolated by filtration and melt at rt. Saturated solution of $NaHCO_3$ (30 mL) was added to the oily mixture. The resulting mixture was extracted with dichloromethane. The organic phase was dried with magnesium sulfate and concentrated to dryness. 1.486 g of a yellow oily solid was obtained.

$^1$H NMR (CDCl$_3$, 400 MHz): δ 7.80 (2H, d, J=7.8 Hz), 7.77-7.74 (1H, m), 7.70-7.63 (3H, m), 7.49 (1H, d, J=7.9 Hz), 7.38 (1H, d, J=7.9 Hz), 6.64 (2H, ddd, J=46.8, J=13.0, J=9.5 Hz), 2.53 (3H, s), 2.46 (3H, s). $^{13}$C NMR. (CDCl$_3$, 100 MHz): δ 139.8, 138.8, 136.0, 134.6, 133.0, 131.4, 131.2, 130.5, 130.4, 129.0, 126.0, 89.9 (d, J=241.4 Hz), 21.1, 19.5. FT-IR (film): 3018, 2958, 1494, 1448, 1259, 1160, 1060, 1029 cm$^{-1}$.

EXAMPLE 5

Preparation of 1-((fluoromethyl)sulfinyl)-4-methylbenzene Starting from methyl p-tolyl sulfide Isolating Each Intermediate

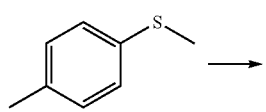

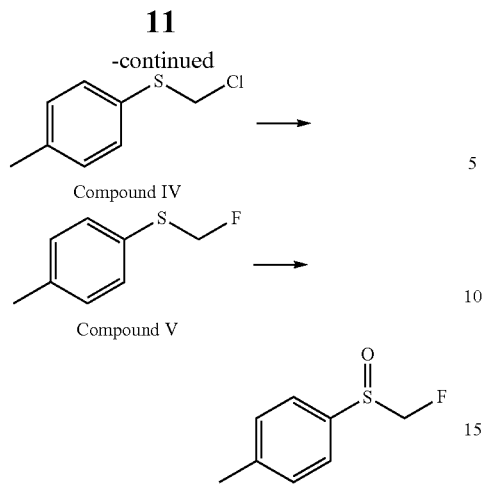

1) Preparation of (chloromethyl)(p-tolyl)sulfane (Compound IV)

Methyl p-tolyl sulfide (75 g, 542.27 mmol) was diluted in chorobenzene (452 mL). N-Chloro Succinimide (NCS) (76.07 g, 1.05 eq) was added in small portions maintaining the temperature between 35° C. and 45° C., under an argon atmosphere. The reaction mixture was stirred at the same temperature range until the reaction was complete. After that time, the solution turned into a suspension. The suspension formed was filtered and the solid was washed with chlorobenzene (50 ml). The filtrate was washed with water (3×225 mL). The resulting organic phase was dried with magnesium sulfate and concentrated. The crude product was purified by distillation to give 102.68 g (100%) of the desired product as yellow oil (bp: 96° C. at 40 Pa).

2) Preparation of (fluoromethyl)(p-tolyl)sulfane (Compound V)

Cesium fluoride (149.55 g, 2 eq) was added to a mixture of PEG400 (90 mL) and acetonitrile (540 mL). The mixture was stirred a few minute under an argon atmosphere and then acetonitrile (90 mL) was removed by distillation. (Chloromethyl)(p-tolyl)sulfane (102.68 g, 492.25 mmol) was added. The reaction mixture was stirred at a temperature between 80° C. and 85° C. until the reaction was complete. The suspension formed, was filtered and the filtrate was concentrated. The crude product was purified by distillation to give 52.09 g (68%) of the desired product as slightly yellow oil (bp: 57° C. at 40 Pa).

3) Preparation of 1-((fluoromethyl)sulfinyl)-4-methylbenzene (Compound VI)

(Fluoromethyl)(p-tolyl)sulfane (52.09 g, 320.06 mmol) was added to a mixture of methanol (250 mL) and water (50 mL). The resulting mixture was cooled to a temperature between 0° C. and 5° C. NBS (68.36 g, 1.2 eq) was added in small portions, maintaining the same temperature range. The reaction mixture was stirred at the same temperature range until the reaction was complete. After that, the reaction mixture was quenched by the addition of $Na_2SO_3$ (10%, 150 mL). The pH of the reaction mixture was adjusted to a value between 7 and 8, with saturated $NaHCO_3$ solution. The mixture was concentrated under vacuum at a temperature between 20° C. and 25° C. The residue was extracted with dichloromethane (200 mL, 150 mL). The combined organic layer was washed with water (2×300 ml) and concentrated to ⅓ of the volume. Heptane (50 mL) was added and then removed by distillation. The crude product was purified by flash chromatography (Ethyl Acetate/Hexane 30:70) to give 48.32 g (88%) of the desired product as a white solid.

EXAMPLE 6

Preparation of (3,4-dimethylphenyl)(fluoromethyl)(p-tolyl)sulfonium tetrafluoroborate

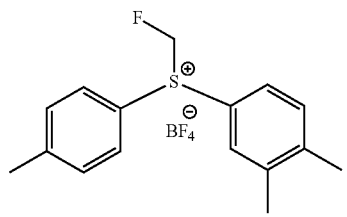

1-((Fluoromethyl)sulfinyl)-4-methylbenzene (576 mg, 3.34 mmol) of example 5 was dissolved in dry diethyl ether (15 mL) under argon atmosphere. O-Xylene (0.445 mL, 1.10 eq) was added to the previous solution. The mixture was cooled to a temperature below −50° C. After stabilizing the temperature below −50° C., trifluoromethanesulfonic anhydride (0.562 mL, 1 eq) was added slowly maintaining the same temperature. The mixture was stirred, until the reaction was complete. $HBF_4$ in diethyl ether solution (54%, 0.921 mL, 2 eq) was added. The resulting suspension was stirred for 30 minutes. The precipitate tetrafluoroborate salt was isolated by filtration and washed with diethyl ether at 0° C. The desired product was obtained as an oily solid (1.42 g).

$^1$H NMR (CDCl$_3$, 400 MHz): δ 7.74 (2H, d, J=8.4 Hz), 7.62 (1H, s), 7.57-7.47 (1H, m), 7.48 (1H, d, J=8.3 Hz), 7.42 (1H, d, J=8.2 Hz), 6.49 (2H, d, J=46.5 Hz), 2.47 (3H, s), 2.37 (3H, s), 2.36 (3H, s). $^{13}$C NMR (CDCl$_3$, 100 MHz): δ 146.5, 145.4, 141.0, 132.4, 132.1, 131.6, 131.0, 128.6, 128.5, 89.9 (d, J=240.2 Hz), 21.5, 19.9, 19.6. FT-IR (film): 2985, 1592, 1492, 1450, 1295, 1228, 1066, 1025 cm$^{-1}$.

EXAMPLE 7

Preparation of (2,5-dimethylphenyl)(fluoromethyl)(p-tolyl)sulfonium tetrafluoroborate

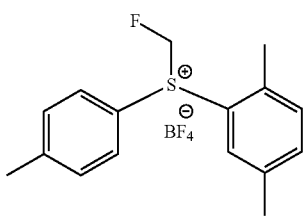

1-((fluoromethyl)sulfinyl)-4-methylbenzene (535 mg, 3.38 mmol) of example 5 was dissolved in dry diethyl ether (15 mL) under an argon atmosphere. P-xylene (0.42 mL, 1.0 eq) was added to the previous solution. The mixture was cooled to a temperature below −50° C. After stabilizing the temperature, trifluoromethanesulfonic anhydride (0.52 mL, 0.92 eq) was added slowly maintaining the same temperature. The mixture was stirred, at the same temperature, until the reaction was complete. $HBF_4$ in diethyl ether solution (54%, 1.29 mL, 2.77 eq) was added. The resulting suspension was stirred for 30 minutes. The precipitate tetrafluoroborate salt was isolated by filtration and washed with diethyl ether at 0° C. The desired product was obtained as a slightly yellow oily solid (2.25 g). after heating at room temperature $^1$H NMR (CDCl$_3$, 400 MHz): δ 7.67 (2H, d, J=8.2 Hz), 7.59 (1H, s), 7.47 (3H, d, J=8.2 Hz), 7.35 (1H, d, J=7.8 Hz), 6.51 (2H, ddd, J=46.0, J=21.4, J=9.4 Hz), 2.51 (3H, s), 2.47 (3H, s), 2.45 (3H, s). $^{13}$C NMR (CDCl$_3$, 100 MHz): δ 146.5, 139.7, 138.4, 135.9, 133.1, 132.2, 131.1, 130.0, 128.5, 119.8, 116.2, 89.0 (d, J=240.5 Hz), 21.5, 20.9, 19.1. FT-IR (film): 1430, 1255, 1072, 1031 cm$^{-1}$.

EXAMPLE 8

Preparation of (fluoromethyl)(isopropylphenyl)(p-tolyl)sulfonium tetrafluoroborate

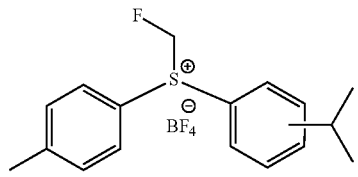

1-((Fluoromethyl)sulfinyl)-4-methylbenzene (738 mg, 4.29 mmol) of example 5 was dissolved in dry diethyl ether (15 mL) under an argon atmosphere. Cumene (0.66 mL, 1.1 eq) was added to the previous solution and then the mixture was cooled to a temperature below −50° C. After stabilizing the temperature, trifluoromethanesulfonic anhydride (0.72 mL, 1 eq) was added slowly maintaining the same temperature. The mixture was stirred, at the same temperature, until the reaction was complete. HBF$_4$ in diethyl ether solution (54%, 1.18 mL, 2 eq) was added. The resulting suspension was stirred for 30 minutes. The precipitate tetrafluoroborate salt was isolated by filtration and washed with diethyl ether at 0° C. The desired product was obtained as a slightly yellow oily solid (2.22 g) after heating at room temperature.

$^1$H NMR (CDCl$_3$, 400 MHz): δ 7.78-7.74 (4H, m), 7.54-7.48 (4H, m), 6.51 (2H, d, J=46.5 Hz), 3.02 (1H, m), 2.48 (3H, s), 1.28 (6H, d, J=6.8 Hz). $^{13}$C NMR (CDCl$_3$, 100 MHz): δ146.4, 132.1, 131.5, 131.3, 130.3, 129.7, 124.7, 90.8 (d, J=240.8 Hz), 34.2, 23.8, 23.4, 21.6.

FT-IR (film): 1592, 1494, 1450, 1388, 1292, 1228, 1180, 1066, 1029 cm$^{-1}$.

EXAMPLE 9

Preparation of (tert-butyl)phenyl)(fluoromethyl)(p-tolyl)sulfonium triflate

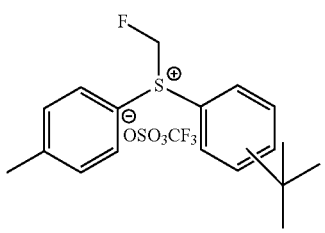

1-((Fluoromethyl)sulfinyl)-4-methylbenzene (624 mg, 3.62 mmol) of example 5 was dissolved in dry diethyl ether (15 mL) under an argon atmosphere. Tert-buthylbenzene (0.561 mL, 1 eq) was added to the previous solution. The mixture was cooled to a temperature below −50° C. After stabilizing the temperature, trifluoromethanesulfonic anhydride (0.61 mL, 1 eq) was added slowly maintaining the same temperature. The mixture was stirred, at the same temperature, until the reaction was complete. The precipitate triflate salt was isolated by filtration and washed with diethyl ether at 0° C. The desired product was obtained as a slightly yellow oily solid (1.089 g) after heating at room temperature, which was a mixture by proton NMR.

EXAMPLE 10

Preparation of (tert-butyl)phenyl)(fluoromethyl)(p-tolyl)sulfonium tetrafluoroborate

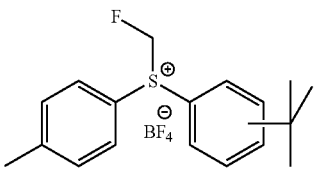

1-((Fluoromethyl)sulfinyl)-4-methylbenzene (495 mg, 2.87 mmol) of example 5 was dissolved in dry diethyl ether (15 mL) under an argon atmosphere. Tert-buthylbenzene (0.445 mL, 1 eq) was added to the previous solution. The mixture was cooled to a temperature below −50° C. After stabilizing the temperature below −50° C., trifluoromethanesulfonic anhydride (0.483 mL, 1 eq) was added slowly maintaining the same temperature. The mixture was stirred, at the same temperature, until the reaction was complete. HBF$_4$ in diethyl ether (54%, 0.791 mL, 2 eq) was added and the resulting suspension was stirred for 30 minutes. The precipitate tetrafluoroborate salt was isolated by filtration and washed with diethyl ether at 0° C. 0.5 g (wet) of the desired product was obtained as a slightly yellow oily solid after heating at room temperature.

$^1$H NMR (CDCl$_3$, 400 MHz): δ 7.78-7.73 (4H, m), 7.53-7.50 (4H, m), 6.38 (2H, d, J=46.1 Hz), 2.51 (3H, s), 1.32 (9H, s). $^{13}$C NMR (CDCl$_3$, 100 MHz): δ 147.0, 132.4, 131.4, 131.1, 130.9, 128.9, 125.3, 117.8, 90.0 (d, J=241.3 Hz), 34.3, 31.2, 21.5.

FT-IR (film): 1498, 1450, 1276, 1230, 1186, 1029 cm$^{-1}$.

EXAMPLE 11

Preparation of (fluoromethyl)(naphthalen-2-yl)(p-tolyl)sulfonium tetrafluoroborate

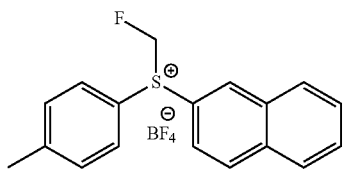

1-((Fluoromethyl)sulfinyl)-4-methylbenzene (481 mg, 2.79 mmol) of example 5 was dissolved in dry diethyl ether (15 mL) under argon atmosphere. Naphthalene (393.8 mg, 1.1 eq) was added to the previous solution and then the mixture was cooled to a temperature below −50° C. After stabilizing the temperature below −50° C., trifluoromethanesulfonic anhydride (0.47 mL, 1 eq) was added slowly maintaining the same temperature. The mixture was stirred, at the same temperature, until the reaction was complete. $HBF_4$ in diethyl ether (54%, 0.77 mL, 2 eq) was added. The resulting suspension was stirred for 30 minutes. The precipitate tetrafluoroborate salt was isolated by filtration and washed with diethyl ether at 0° C. The desired product was obtained as a yellow oily solid (1.873 g) after heating at room temperature.

$^1$H NMR (CDCl$_3$, 400 MHz): δ 8.33 (1H, d, J=8.3 Hz), 8.26 (1H, d, J=8.2 Hz), 8.04-8.01 (2H, m), 7.82-7.78 (3H, m), 7.76-7.69 (2H, m), 7.49 (2H, d, J=8.3 Hz), 6.65 (2H, ddd, J=46.8, J=29.7, J=9.5 Hz), 2.46 (3H, s). $^{13}$C NMR. (CDCl$_3$, 100 MHz): δ 147.0, 135.8, 134.3, 132.3, 131.4, 131.3, 130.6, 130.0, 129.6, 128.3, 121.7, 116.5, 115.8, 90.7 (d, J=89.6 Hz), 21.4. FT-IR (film): 1592, 1494, 1450, 1448, 1267, 1066, 1027 cm$^{-1}$.

EXAMPLE 12

Preparation of (fluoromethyl)(2,3,4,5-tetramethylphenyl)(p-tolyl)sulfonium triflate

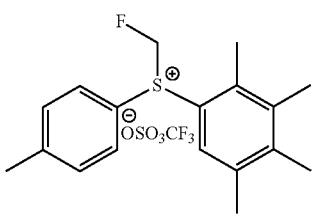

1-((Fluoromethyl)sulfinyl)-4-methylbenzene (3 g, 17.42 mmol) of example 5 was dissolved in dry diethyl ether (100 ml) under nitrogen atmosphere. 1,2,3,4-Tetramethylbenzene (2.60 mL, 1.0 eq) was added to the previous solution and then the mixture was cooled to a temperature below −10° C. Trifluoromethanesulfonic anhydride (2.93 mL, 1 eq) was added slowly maintaining the same temperature. The mixture was stirred at the same temperature, until the reaction was complete. A pink suspension was formed and after 3 hours, turned into a light grey suspension. The precipitate triflate salt was isolated by filtration, washed with diethyl ether at 0° C. and dried under vacuum at a temperature below 30° C. 5.68 g (79.44%) of the desired product was obtained as a white solid.

$^1$H NMR (CDCl$_3$, 400 MHz): δ 7.68 (2H, d, J=8.0 Hz), 7.47-7.42 (3H, m), 6.53 (2H, ddd, J=46.8, J=22.5, J=9.2 Hz), 2.48 (3H, s), 2.45 (3H, s), 2.37 (3H, s), 2.29 (3H, s), 2.28 (3H, s). $^{13}$C NMR (CDCl$_3$, 100 MHz): δ 146.0, 143.7, 139.3, 138.1, 137.0, 132.1, 130.9, 128.2, 128.1, 122.1, 118.9, 117.4, 116.6, 89.8 (d, J=240.0 Hz), 21.6, 21.1, 17.6, 16.88, 16.80. FT-IR (KBr): 3054, 3004, 2960, 2888, 1592, 1459, 1272, 1251, 1224, 1159, 1066, 1027.

EXAMPLE 13

Preparation of (fluoromethyl)(2,3,4,5-tetramethylphenyl)(p-tolyl)sulfonium tetrafluoroborate

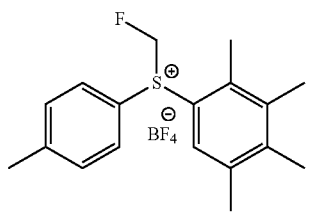

1-((Fluoromethyl)sulfinyl)-4-methylbenzene (1.5 g, 8.71 mmol) of example 5 was dissolved in dry diethyl ether (50 ml) under an nitrogen atmosphere. 1,2,3,4-Tetramethylbenzene (1.3 mL, 1 eq) was added to the previous solution and then the mixture was cooled to a temperature below −10° C. Trifluoromethanesulfonic anhydride (1.46 mL, 1 eq) was added maintaining the same temperature. The mixture was stirred at the same temperature, until the reaction was complete. A pink suspension was formed and after 3 hours turned into a light grew suspension. The precipitate triflate salt was isolated by filtration and washed with diethyl ether at 0° C. The solid was dissolved in dichloromethane (20 ml) and the resulting organic solution was washed with a solution of NaBF$_4$ 1N (6×30 ml). The organic phase was dried with magnesium sulfate and concentrated to dryness. 1.67 g of the desired product was obtained as a white solid.

$^1$H NMR (CDCl$_3$, 400 MHz): δ 7.67 (2H, d, J=8.2 Hz), 7.47-7.42 (3H, m), 6.46 (2H, ddd, J=17.2, J=9.4 Hz), 2.48 (3H, s), 2.45 (3H, s), 2.37 (3H, s), 2.29 (3H, s), 2.27 (3H, s). $^{13}$C NMR (CDCl$_3$, 100 MHz): δ 146.0, 143.7, 139.3, 138.1, 137.1, 132.1, 130.9, 128.2, 128.1, 117.4, 116.6, 89.5 (d, J=239.2 Hz), 21.6, 21.1, 17.6, 16.89, 16.82. FT-IR (KBr): 3039, 2975, 2962, 1590, 1492, 1450, 1066, 1037, 1008.

EXAMPLE 14

Preparation of fluticasone 17-propionate in dichloromethane Using (2,5-dimethylphenyl)(fluoromethyl)(phenyl)sulfonium tetrafluoroborate as Reagent

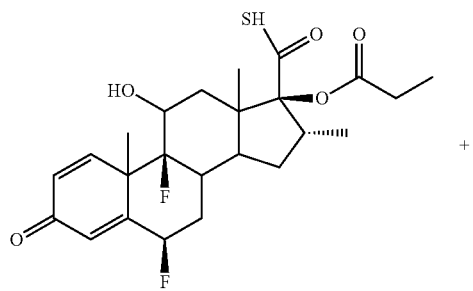

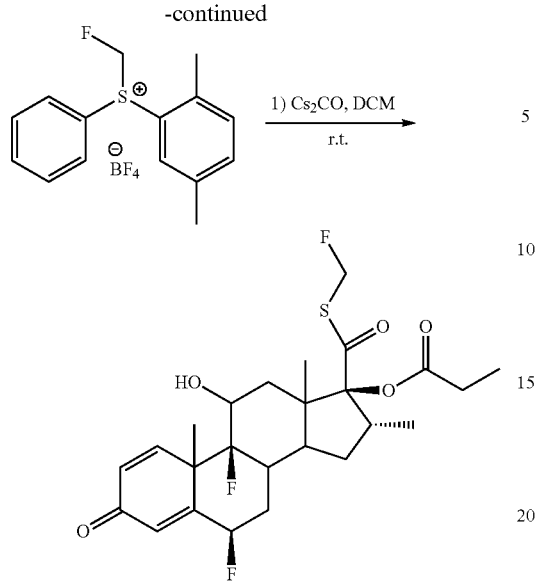

The 17-propionate carbothioic acid (100 mg, 0.21 mmol) of example 4 was dissolved in dichloromethane (7 mL) under an argon atmosphere. Cesium carbonate (0.041 mg, 0.6 eq) and (2,5-dimethylphenyl)(fluoromethyl)(phenyl)sulfonium tetrafluoroborate (131 mg, 1.5 eq) was added. The reaction mixture was stirred overnight and then quenched with water (5 mL). The resulting mixture was extracted with dichloromethane (3×3 mL). The combined organic phase was dried with anhydrous MgSO$_4$ and concentrated. The residue was purified by flash chromatography (ethyl acetate/hexane 1:1) and it was crystallized from ethyl acetate and hexane to afford 0.085 g (79%) of the desired product as a white solid. The $^1$H-NMR and $^{13}$C-NMR spectra were identical to those of fluticasone propionate.

EXAMPLE 15

Preparation of fluticasone 17-propionate in dichloromethane Using (3,4-dimethylphenyl)(fluoromethyl)(phenyl)sulfonium tetrafluoroborate as Reagent

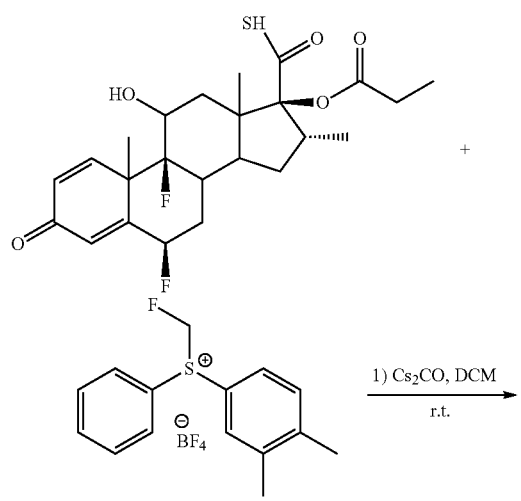

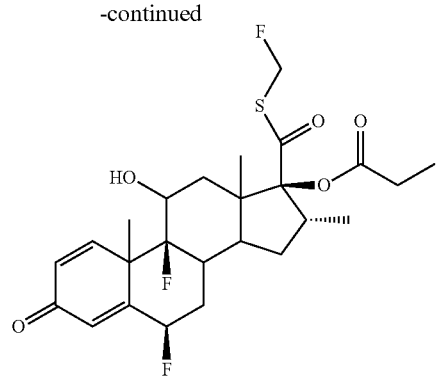

The 17-propionate carbothioic acid (0.100 g, 0.21 mmol) of example 3 was dissolved in CH$_2$Cl$_2$ (1.4 mL) at r.t. Cesium carbonate (0.041 g, 0.6 eq) and (3,4-dimethylphenyl)(fluoromethyl)(phenyl)sulfonium tetrafluoroborate of example 3 (0.131 g, 1.5 eq) was added. The reaction mixture was stirred overnight, quenched with water (5 mL) and extracted with CH$_2$Cl$_2$ (3×3 mL). The combined organic phases were dried (anhydrous MgSO$_4$) and concentrated. The residue was purified by flash chromatography (ethyl acetate hexane 1:1) and then crystallized from ethyl acetate and hexane to afford 0.092 g (87%) of the desired product as a white solid. The $^1$H-NMR and $^{13}$C-NMR spectra were identical to those of fluticasone propionate.

EXAMPLE 16

Preparation of fluticasone 17-propionate in dichloromethane Using (fluoromethyl)(2,3,4,5-tetramethylphenyl)(p-tolyl)sulfonium triflate as Reagent

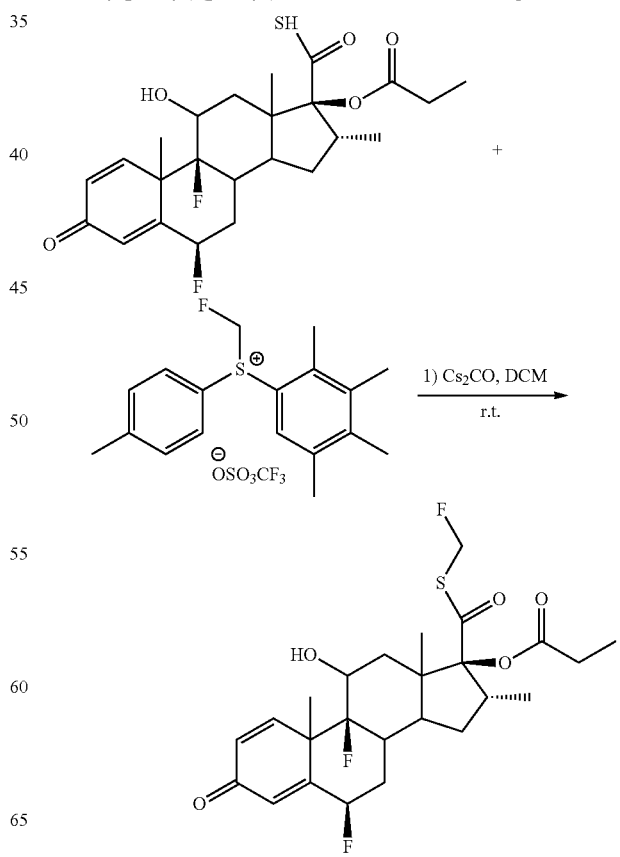

The 17-propionate carbothioic acid (0.5 g, 1.07 mmol) of example 12 was dissolved in dichloromethane (7 mL). Cesium carbonate (208.6 mg, 0.6 eq) was added and the resulting suspension was stirred for 30 minutes at room temperature. (Fluoromethyl)(2,3,4,5-tetramethylphenyl)(p-tolyl)sulfonium triflate (700.28 mg, 1.5 eq) was added. The reaction mixture was stirred at room temperature until the reaction is complete. Heptane (25 mL) was added and the resulting suspension was stirred for 15 minutes at the same temperature. The solid was isolated by filtration and dried under vacuum at a temperature below 35° C. 1.71 g of product was obtained. The product was recrystallized from a mixture of acetone and water. The salts are purged during this recrystallization. 0.530 g of the desired product was obtained as a white solid. The $^1$H-NMR and $^{13}$C-NMR spectra were identical to those of fluticasone propionate.

EXAMPLE 17

Preparation of fluticasone 17-propionate in dichloromethane Using (fluoromethyl)(2,3,4,5-tetramethylphenyl)(p-tolyl)sulfonium tetrafluoroborate as Reagent

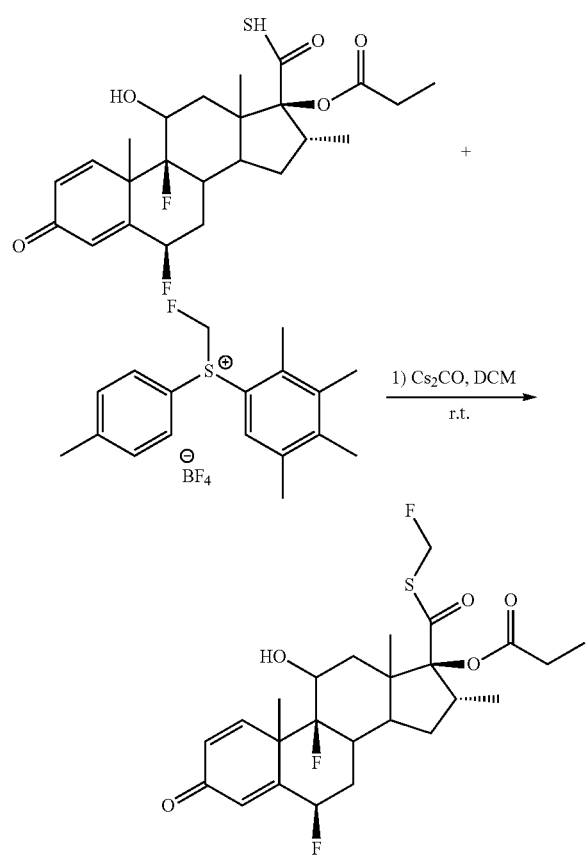

The 17-propionate carbothioic acid (0.5 g, 1.07 mmol) of example 13 was dissolved in dichloromethane (7 mL). Cesium carbonate (208.6 mg, 0.6 eq) was added and the resulting suspension was stirred for 30 minutes at room temperature. (Fluoromethyl)(2,3,4,5-tetramethylphenyl)(p-tolyl)sulfonium tetrafluoroborate (600.61 mg, 1.5 eq) was then added. The reaction mixture was stirred at room temperature until the reaction was complete and heptane then added (20 mL). The resulting suspension was stirred for 10 minutes. The solid was isolated by filtration and dried under vacuum at a temperature below 35° C. whereafter 0.85 g of product was obtained. The product was recrystallized from a mixture of acetone and water. The salts are purged during this recrystallization. 0.41 g of product was obtained as white solid. The $^1$H NMR and $^{13}$C-NMR spectra were identical to those of fluticasone propionate.

EXAMPLE 18

Preparation of fluticasone 17-furoate in dichloromethane Using (2,5-dimethylphenyl)(fluoromethyl)(phenyl)sulfonium tetrafluoroborate as Reagent

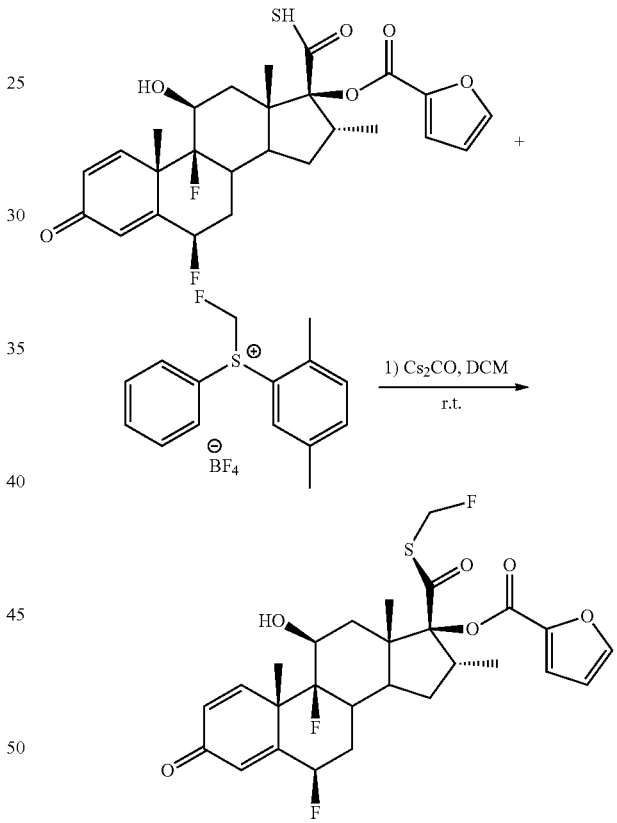

The 17-furoate carbothioic acid (0.100 g, 0.20 mmol) was suspended in CH$_2$Cl$_2$ (1.4 mL) at r.t. Cesium carbonate (0.039 g, 0.55 eq) and (2,5-dimethylphenyl)(fluoromethyl)(phenyl)sulfonium tetrafluoroborate of example 4 (0.121 g, 1.5 eq) was added. The reaction mixture was stirred overnight, quenched with water (5 mL) and extracted with CH$_2$Cl$_2$ (3×3 mL). The combined organic phase was dried with anhydrous MgSO$_4$ and concentrated. The residue was purified by flash chromatography (ethyl acetate/hexane 1:1) and crystallised from dichloromethane and hexane to afford 0.076 g (76%) of the desired product as a white solid. The $^1$H-NMR and $^{13}$C-NMR spectra were identical to those of Fluticasone furoate.

EXAMPLE 19

Preparation of fluticasone 17-furoate in dichloromethane Using (3,4-dimethylphenyl)(fluoromethyl)(phenyl)sulfonium tetrafluoroborate as Reagent

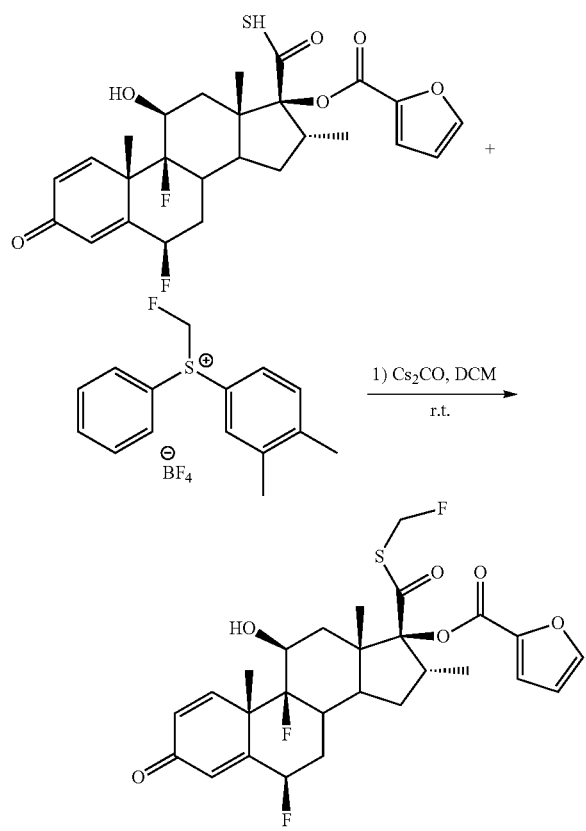

The 17-furoate carbothioic acid (0.100 g, 0.20 mmol) was suspended in CH$_2$Cl$_2$ (1.4 mL) at r.t. Cesium carbonate (0.039 g, 0.55 eq) and (3,4-dimethylphenyl)(fluoromethyl)(phenyl)sulfonium tetrafluoroborate of example 3 (0.121 g, 1.5 eq) was added. The reaction mixture was stirred overnight, quenched with water (5 mL) and extracted with CH$_2$Cl$_2$ (3×3 mL). The combined organic phase was dried with anhydrous MgSO$_4$ and concentrated. The residue was purified by flash chromatography (ethyl acetate/hexane 1:1) and crystallised from dichloromethane and hexane to afford 0.088 g (83%) of the desired product as a white solid. The $^1$H-NMR and $^{13}$C-NMR spectra were identical to those of Fluticasone furoate.

EXAMPLE 20

Preparation of fluticasone 17-furoate in dichloromethane Using (fluoromethyl)(2,3,4,5-tetramethylphenyl)(p-tolyl)sulfonium triflate as Reagent

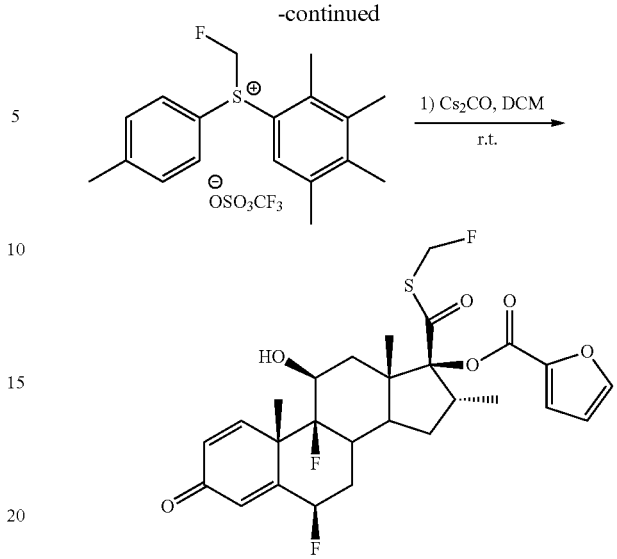

The 17-Propionate carbothioic acid (0.5 g, 989 mmol) was suspended in dichloromethane (7 mL). Cesium carbonate (193.35 mg, 0.6 eq) was added and the resulting suspension was stirred for 30 minutes at room temperature. (Fluoromethyl)(2,3,4,5-tetramethylphenyl)(p-tolyl)sulfonium triflate of example 12 (649.0 mg, 1.5 eq) was added. The reaction mixture was stirred at room temperature until the reaction was complete. Heptane (mL) was added and resulting suspension was stirred for 30 minutes at the same temperature. The solid was isolated by filtration and dried under vacuum at a temperature below 35° C. The product (1.6 g) was recrystallized from a mixture of acetone and water. The salts are purged during this recrystallization. 0.46 g o product was obtained as white solid. The $^1$H-NMR and $^{13}$C-NMR spectra were identical to those of fluticasone furoate.

EXAMPLE 21

Preparation of monochloromethyl phenyl sulfoxide Starting from methylphenylsulfide Isolating Each Intermediate

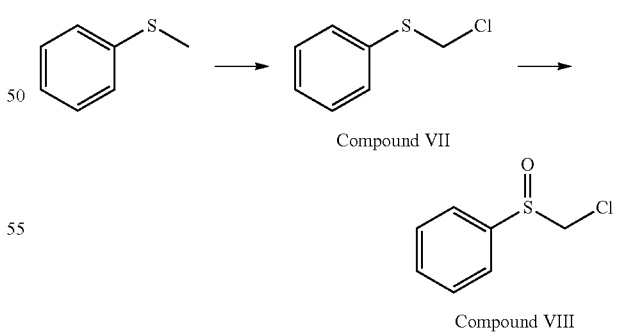

1) Preparation of chloromethyl phenyl sulphide Starting from methylphenylsulfide (Compound VII)

Methylphenylsulfide (100 g, 805.13 mmol) was diluted in chorobenzene (602 mL). N-Chloro Succinimide (NCS) (112.89 g, 845.39 mmol) was added in small portions maintaining the temperature between 35° C. and 45° C., under an argon atmosphere. After 3 hours, the suspension formed was filtered and washed with chlorobenzene (50 mL). The filtrate was washed with water (3×300 mL). The resulting organic phase was dried with magnesium sulfate and concentrated. The crude product was purified by distillation to give 98 g (77%) of the desired product as yellow oil (bp: 62° C. at 40 Pa).

2) Preparation of chloromethyl phenyl sulfoxide (Compound VIII)

Chloromethyl phenyl sulfide (3 g, 18.9 mmol) was dissolved in a mixture of methanol (15 mL) and water (3 mL). The resulting mixture was cooled to a temperature between 0° C. and 5° C. NBS (4.04 g, 1.2 eq) was added in small portions, maintaining the same temperature range. The reaction mixture was stirred within the same temperature range until the reaction was complete. Thereafter, the reaction mixture was quenched by the addition of $Na_2SO_3$ solution (10%, 15 mL). The pH of the reaction mixture was adjusted to a value between 7 and 8, with saturated $NaHCO_3$ solution. The resulting mixture was extracted with dichloromethane (3×50 mL). The combined organic layer was dried with anhydrous $MgSO_4$ and concentrated. The crude product was purified by medium pressure chromatography (Ethyl Acetate/Hexane 2:8) to give 1.381 g (42%) of the desired product as a colourless liquid. $^1$H NMR (CDCl$_3$, 400 MHz): δ 7.71-7.69 (2H, m), 7.57-7.56 (3H, m), 4.41 (2H, ABQ, J=10.8 Hz). $^{13}$C NMR (CDCl$_3$, 100 MHz): δ 140.8, 132.1, 126.3, 124.8, 61.3. FT-IR (NaCl): 3058, 3004, 2935, 1472, 1444, 1384, 1218, 1085, 1052 cm$^{-1}$.

EXAMPLE 22

Preparation of (chloromethyl)(phenyl)(2,3,4,5-tetramethylphenyl)sulfonium triflate

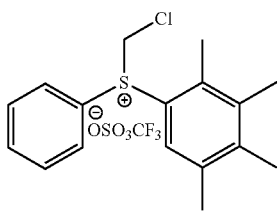

Chloromethyl phenyl sulfoxide (12 g, 68.71 mmol) of example 21 was dissolved in dry diethyl ether (100 mL) under an argon atmosphere. 1,2,3,4-Tetramethylbenzene (10.3 mL, 1 eq) was added to the previous solution and then the mixture was cooled to a temperature between 5° C. and 0° C. After stabilizing the temperature, trifluoromethanesulfonic anhydride (11.5 mL, 1 eq) was added slowly maintaining the same temperature. The mixture was stirred until the reaction was complete. The precipitate triflate salt formed was isolated by filtration and washed with diethyl ether at 0° C. (50 mL). 16.18 g (57.4%) of the desired product was obtained as a white solid. mp: 125-127° C.
$^1$H NMR (CDCl$_3$, 400 MHz): δ 7.90 (2H, d, J=7.7 Hz), 7.73-7.66 (4H, m), 6.99 (1H, d, J=11.0 Hz), 5.94 (1H, d, J=11.0 Hz), 2.51 (3H, s), 2.42 (3H, s), 2.29 (3H, s), 2.28 (3H, s). $^{13}$C NMR (CDCl$_3$, 100 MHz): δ 144.2, 139.1, 138.8, 137.2, 134.8, 131.4, 130.8, 127.5, 123.0, 116.9, 52.4, 20.9, 17.6, 16.9, 16.8. FT-IR (KBr): 3023, 2954, 1710, 1585, 1479, 1448, 1276, 1245, 1159, 1029 cm$^{-1}$.

EXAMPLE 23

Preparation of (chloromethyl)(phenyl)(2,3,4,5-tetramethylphenyl)sulfonium tetrafloroborate

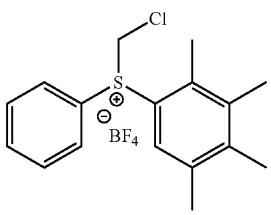

The triflate salt (6 g) of example 22 was dissolved in dichloromethane (30 mL). The solution was washed $NaBF_4$ solution (1M, 5×80 mL and 2×50 mL). The resulting organic layer was dried with sodium sulfate and concentrated to dryness. 4.61 g of white solid was obtained. (Yield: 76.8% w/w); mp: 171-172° C.
$^1$H NMR (CDCl$_3$, 400 MHz): δ 7.86 (2H, d, J=7.5 Hz), 7.74-7.61 (4H, m), 5.82 (1H, d, J=11.3 Hz), 5.80 (1H, d, J=11.3 Hz), 2.51 (3H, s), 2.42 (3H, s), 2.30 (3H, s), 2.28 (3H, s). $^{13}$C NMR (CDCl$_3$, 100 MHz): δ 144.2, 139.1, 138.9, 137.2, 134.8, 131.5, 130.7, 127.4, 122.8, 116.6, 52.1, 20.9, 17.5, 16.9, 16.8. FT-IR (KBr): 3099, 3058, 2989, 1581, 1469, 1448, 1409, 1286, 1222, 1056 cm$^{-1}$.

EXAMPLE 24

Preparation of (chloromethyl)(3,4-dimethylphenyl)(phenyl)sulfonium triflate

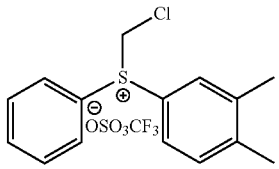

Chloromethyl phenyl sulfoxide (300 mg, 1.94 mmol) of example 21 was dissolved in dry diethyl ether (7.5 mL) under an argon atmosphere. O-Xylene (227 mg, 1.1 eq) was added to the previous solution and the mixture cooled to a temperature below −60° C. After stabilizing the temperature, trifluoromethanesulfonic anhydride (0.326 mL, 1 eq) was added slowly maintaining the same temperature. The mixture was stirred until the reaction was complete. The precipitated triflate salt was isolated by filtration and washed with diethyl ether at 0° C. (50 mL). 0.602 g (75%) of the desired product was obtained as a oily solid. $^1$H NMR (CDCl$_3$, 400 MHz): δ 7.93 (2H, d, J=7.9 Hz), 7.74-7.65 (5H, m), 7.44 (1H, d, J=8.1 Hz), 5.86 (2H, s), 2.35 (6H, s). $^{13}$C NMR (CDCl$_3$, 100 MHz): δ 146.0, 141.3, 135.1, 132.0, 132.6, 131.6, 131.4, 130.9, 128.6, 122.5, 121.5, 118.3, 117.7, 52.3, 20.0, 19.7. FT-IR (NaCl): 3023, 2956, 1483, 1448, 1226, 1027 cm$^{-1}$.

EXAMPLE 25

Preparation of (chloromethyl)(2,5-dimethylphenyl)(phenyl)sulfonium triflate

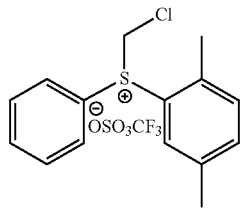

Chloromethyl phenyl sulfoxide (300 mg, 1.94 mmol) of example 21 was dissolved in dry diethyl ether (7.5 mL) under an argon atmosphere. p-Xylene (227 mg, 1.1 eq) was added to the previous solution and the mixture was cooled to a temperature below −60° C. After stabilizing the temperature, trifluoromethanesulfonic anhydride (0.326 mL, 1 eq) was added slowly maintaining the same temperature. The mixture was stirred until the reaction was complete. The precipitate triflate salt formed was isolated by filtration and washed with cold diethyl ether at 0° C. 602 mg (75%) of the desired product was obtained as a oily solid after heating at room temperature.

δ 7.91 (2H, d, J=7.9 Hz), 7.85 (1H, s), 7.73-7.64 (3H, m), 7.44 (1H, d, J=7.8 Hz), 7.33 (1H, d, J=7.9 Hz), 5.97 (2H, s), 2.52 (3H, s), 2.44 (3H, s). $^{13}$C NMR (CDCl$_3$, 100 MHz): δ 140.3, 138.6, 136.1, 135.1, 132.7, 131.5, 131.0, 129.3, 122.2, 121.8, 120.3, 118.7, 51.6, 20.7, 19.3. FT-IR (NaCl): 3025, 2956, 1494, 1448, 1251, 1168, 1029 cm$^{-1}$.

EXAMPLE 26

Preparation of (chloromethyl)(isopropylphenyl)(phenyl)sulfonium triflate

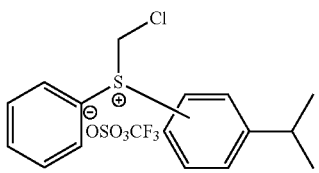

Chloromethyl phenyl sulfoxide (170 mg, 1.1 mmol) of example 21 was dissolved in dry diethyl ether (5 mL) under an argon atmosphere. Cumene (145 mg, 1.1 eq) was added to the previous solution and the mixture was cooled to a temperature below −60° C. After stabilizing the temperature, trifluoromethanesulfonic anhydride (0.184 mL, 1 eq) was added slowly maintaining the same temperature. The mixture was stirred until the reaction was complete. The orange precipitated triflate salt was quickly filtered at −60° C. affording 0.399 g as orange viscous oil after heating at room temperature, which was a mixture by proton NMR.

EXAMPLE 27

Preparation of (4-(tert-butyl)phenyl)(chloromethyl)(phenyl)sulfonium triflate

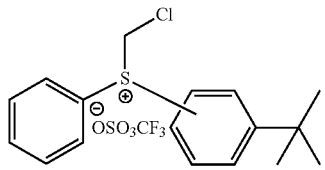

Chloromethyl phenyl sulfoxide (200 mg, 1.29 mmol) of example 21 was dissolved in dry diethyl ether (7.5 mL) under an argon atmosphere. tert-Butyl benzene (0.191 g, 1.1 eq) was added to the previous solution and then the mixture was cooled to a temperature below −60° C. After stabilizing the temperature, trifluoromethanesulfonic anhydride (0.217 mL, 1 eq) was added slowly maintaining the same temperature. The mixture was stirred until the reaction was complete. The orange precipitated triflate salt was quickly filtered at −60° C. affording 0.487 g as red viscous oil after heating at room temperature, which was a mixture by proton NMR.

EXAMPLE 28

Preparation of (chloromethyl)(naphthalen-2-yl)(phenyl)sulfonium triflate

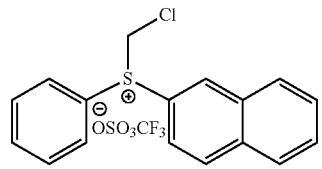

Chloromethyl phenyl sulfoxide (200 mg, 1.29 mmol) of example 21 was dissolved in dry diethyl ether (7.5 mL) under an argon atmosphere. Naphthalene (0.182 g, 1.1 eq) was added to the previous solution and then the mixture was cooled to a temperature below −60° C. After stabilizing the temperature, trifluoromethanesulfonic anhydride (0.217 mL, 1 eq) was added slowly maintaining the same temperature. The mixture was stirred until the reaction was complete. After 4 h at −60° C. the green precipitated triflate salt was quickly filtered at −60° C. affording 0.402 g (71%) of a oily solid after heating at room temperature,.

$^1$H NMR (CDCl$_3$, 400 MHz): δ 8.37 (1H, d, J=7.6 Hz), 8.25 (2H, dd, 2.3 Hz), 8.01-7.97 (4H, m), 7.83-7.62 (5H, m), 6.10 (2H, s). $^{13}$C NMR (CDCl$_3$, 100 MHz): δ 136.0, 135.2, 134.3, 131.6, 131.4, 131.1, 131.0, 130.1, 129.7, 126.6, 121.8, 121.6, 117.2, 52.1. FT-IR (NaCl): 3016, 2948, 1259, 1226, 1170, 1029, 912 cm$^{-1}$.

EXAMPLE 29

Preparation of 1-((chloromethyl)sulfinyl)-4-methylbenzene Starting from methyl p-tolyl sulfide Isolating Each Intermediate

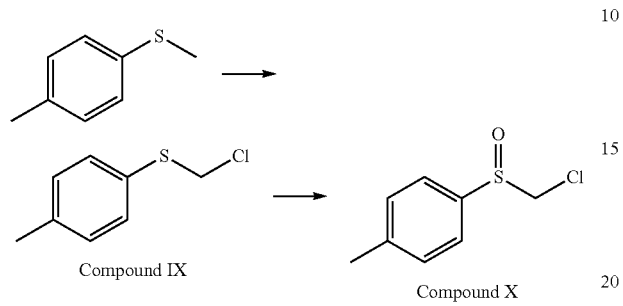

Compound IX

Compound X

1) Preparation of (chloromethyl)(p-tolyl)sulfane (Compound IX)

Methyl p-tolyl sulfide (75 g, 542.27 mmol) was diluted in chorobenzene (452 mL). N-Chloro Succinimide (NCS) (76.07 g, 1.05 eq) was added in small portions maintaining the temperature between 35° C. and 45° C., under an argon atmosphere. The reaction mixture was stirred within the same temperature range until the reaction was complete. Thereafter, a solid separated out from the solution. The suspension was filtered, and the solid washed with chlorobenzene (50 ml). The filtrate was washed with water (3×225 mL). The resulting organic phase was dried with anhydrous magnesium sulfate and concentrated. The crude product was purified by distillation to give 102.68 g (100%) of the desired product as yellow oil (bp: 96° C. at 40 Pa).

2) Preparation of 1-((chloromethyl)sulfinyl)-4-methylbenzene (Compound X)

(Choromethyl)(p-tolyl)sulfane (10 g, 57.91 mmol) was added to a mixture of methanol (50 mL) and water (10 mL). The resulting mixture was cooled to a temperature between 0° C. and 5° C. NBS (12.37 g, 1.2 eq) was added in small portions, maintaining the same temperature range. The reaction mixture was stirred within the same temperature range until the reaction was complete. Thereafter, the reaction mixture was quenched by the addition of $Na_2SO_3$ (10%, 30 mL). The pH of the reaction mixture was adjusted to a value between 7 and 8, with saturated $NaHCO_3$ solution. The mixture was concentrated under vacuum at a temperature between 20° C. and 25° C. and then extracted with dichloromethane (40 mL, 30 mL). The combined organic layer was washed with water (2×60 ml) and concentrated to ⅓ of the volume. Heptane (10 mL) was added and then removed by distillation. The crude product was purified by flash chromatography (Ethyl Acetate/Hexane 30:70) to give 9.78 g (89.51%) of the desired product as a white solid.

EXAMPLE 30

Preparation of (chloromethyl)(2,3,4,5-tetramethylphenyl)(p-tolyl)sulfonium triflate

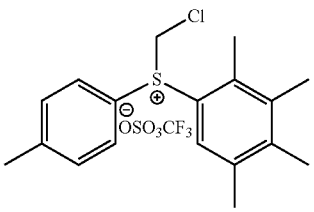

1-((chloromethyl)sulfinyl)-4-methylbenzene (500 mg, 2.65 mmol) of example 29 was dissolved in dry diethyl ether (5 mL) under an argon atmosphere. 1,2,3,4-Tetramethylbenzene (0.40 mL, 1 eq) was slowly added to the previous solution and then the mixture was cooled to a temperature between 5° C. and 0° C. After stabilizing the temperature, trifluoromethanesulfonic anhydride (0.45 mL, 1 eq) was added maintaining the same temperature. The mixture was stirred until the reaction was complete. The precipitated triflate salt was isolated by filtration and washed with diethyl ether (5 mL) at 0° C. 1.12 g (89.74%) of the desired product was obtained as a white solid. Mp=28-30° C.

$^1$H NMR (CDCl$_3$, 400 MHz): δ 7.74 (2H, d, J=8.2 Hz), 7.58 (1H, s), 7.46 (2H, d, J=8.1 Hz), 5.84 (2H, ABQ, J=10.9 Hz), 2.49 (3H, s), 2.44 (3H, s), 2.39 (3H, s), 2.28 (3H, s), 2.26 (3H, s). $^{13}$C NMR (CDCl$_3$, 100 MHz): δ 146.5, 143.9, 139.1, 138.6, 137.0, 132.2, 130.7, 127.1, 52.0, 21.6, 20.8, 17.4, 16.8, 16.7. FT-IR (KBr): 3021, 2956, 1450, 1409, 1288, 1243, 1189, 1164, 1151, 1029 cm$^{-1}$.

EXAMPLE 31

Preparation of (chloromethyl)(2,3,4,5-tetramethylphenyl)(p-tolyl)sulfonium tetrafluoroborate

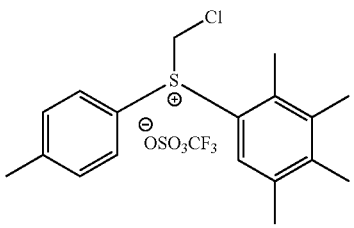

1-((Chloromethyl)sulfinyl)-4-methylbenzene (130 mg, 0.69 mmol) from example 29 was dissolved in dry diethyl ether (4.5 mL). 1,2,3,4-Tetramethylbenzene (102 mg, 1.1 eq) was added. The solution was cooled to a temperature below −60° C. After stabilizing the temperature, trifluoromethanesulfonic anhydride (0.115 mL, 0.69 mmol) was slowly added maintaining the same temperature. After 4 h at −60° C., a solution of HBF$_4$ in diethyl ether (54%, 0.168 mL, 1.5 eq) was added. The resulting mixture was stirred for 30 min. The precipitate tetrafluoroborate salt was quickly filtered at −60° C. affording 0.242 g (89%) as a white solid. Mp=224° C.

$^1$H NMR (DMSO-d$_6$, 400 MHz): δ 7.97 (2H, d, J=8.4 Hz), 7.75 (1H, s), 7.60 (2H, d, J=8.2 Hz), 6.34 (2H, ABQ, J=9.8 Hz), 2.51 (3H, s), 2.43 (3H, s), 2.36 (3H, s), 2.27 (3H, s), 2.26 (3H, s). $^{13}$C NMR (DMSO-d$_6$, 100 MHz): δ 145.8, 142.9, 138.6, 137.3, 137.0, 131.7, 130.8, 126.6, 120.2, 119.3, 51.2, 21.0, 20.4, 17.2, 16.45, 16.43. FT-IR (KBr): 3043, 2967, 1496, 1446, 1407, 1288, 1247, 1220, 1195, 1076, 1049, 1031 cm$^{-1}$.

EXAMPLE 32

Preparation of bromomethyl phenyl sulfoxide Starting from methylphenylsulfide Isolating Each Intermediate

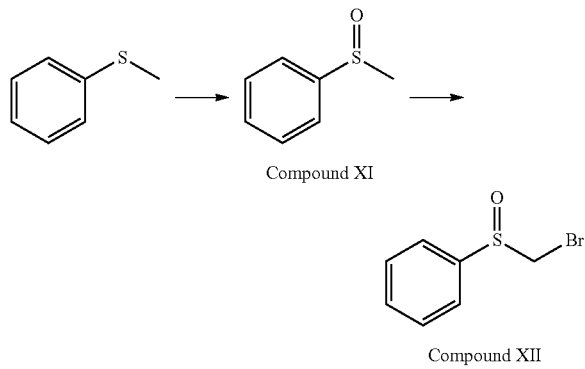

Compound XI

Compound XII

1) Preparation of methylphenylsulfoxide (Compound XI)

Methyl phenyl sulphide (20 g, 161.03 mmol) was added to a mixture of methanol (100 ml) and water (20 mL). NBS (34.39 g, 1.2 eq) was added in portions maintaining the temperature between 0° and 5° C. The mixture was stirred at the same temperature until the reaction was complete. Thereafter, the reaction mixture was quenched by the addition of Na$_2$SO$_3$ (10%, 60 ml). The pH of the resulting reaction mixture was adjusted to a value between 7 and 8 with saturated NaHCO$_3$ solution. The mixture was concentrated under vacuum at a temperature between 20° C. and 25° C. The residue was extracted with dichloromethane (2×125 mL). The combined organic layer was washed with water (2×125 mL) and concentrated to ⅓ of the volume. Heptane (20 mL) was added and then removed by distillation to give 21.64 g (95.9%) of the desired product as colourless oil.

2) Preparation of bromomethyl phenyl sulfoxide (Compound XII)

Methyl phenyl sulfoxide (21.644 g, 154.4 mmol) was dissolved in anhydrous pyridine (27.4 mL, 2.2 eq) and dry acetonitrile (100 mL). The solution was cooled to −40° C. under an argon atmosphere. A solution of bromine (49.4 g, 2 eq) in dry acetonitrile (50 mL) was added slowly, maintaining the same temperature. The mixture was stirred at −40° C. for 1 h and then overnight at room temperature. The solvent was evaporated under vacuum and the residue was dissolved in dichloromethane. The organic layer was washed with Na$_2$S$_2$O$_3$ 20%, dried over anhydrous Na$_2$SO$_4$ and concentrated to dryness.

The crude material was purified by flash column chromatography (ethyl acetate:hexane 20:80) to give 16,989 g of yellow oil (yield 49%).

EXAMPLE 33

Preparation of (bromomethyl)(phenyl)(2,3,4,5-tetramethylphenyl)sulfonium triflate

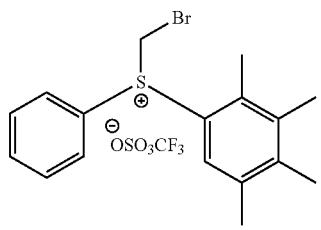

Bromomethyl phenyl sulfoxide (500 mg, 2.29 mmol) of example 32 was dissolved in dry diethyl ether (15 mL) under an argon atmosphere. 1,2,3,4-Tetramethylbenzene (339 mg, 1.09 eq) was added to the previous solution and then the mixture cooled to a temperature below −60° C. After stabilizing the temperature, trifluoromethanesulfonic anhydride (0.385 ml, 1.0 eq) was added slowly, maintaining the same temperature. The mixture was stirred until the reaction was complete. The precipitated triflate salt formed was isolated by filtration, washed with diethyl ether at 0° C. and dried under vacuum. 0.779 g (70%) of the desired product was obtained as a white solid. mp: 115-116° C.

$^1$H NMR (CDCl$_3$, 400 MHz): δ 7.93 (2H, d, J=7.7 Hz), 7.71-7.64 (4H, m), 5.80 (1H, d, J=9.9 Hz), 5.69 (1H, d, J=10.0 Hz), 2.51 (3H, s), 2.42 (3H, s), 2.28 (3H, s), 2.27 (3H, s). $^{13}$C NMR (CDCl$_3$, 100 MHz): δ 144.1, 139.0, 138.9, 137.0, 131.4, 130.6, 127.1, 124.3, 118.0, 35.2, 20.8, 17.5, 16.9, 16.8. FT-IR (KBr): 3075, 3018, 2946, 1481, 1452, 1392, 1263, 1222, 1197, 1159, 1031 cm$^{-1}$.

EXAMPLE 34

Preparation of (bromomethyl)(phenyl)(2,3,4,5-tetramethylphenyl)sulfonium tetrafluoroborate

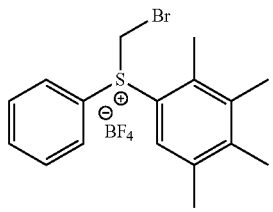

Bromomethyl phenyl sulfoxide (1 g, 4.58 mmol) of example 32 was dissolved in dry diethyl ether (30 mL) under an argon atmosphere. 1,2,3,4-tetramethylbenzene (0.678 g, 1.09 eq) was added to the previous solution and then the mixture was cooled to a temperature below −60° C. After stabilizing the temperature, trifluoromethanesulfonic anhydride (0.77 mL, 1 eq) was added slowly, maintaining the same temperature. The mixture was stirred until the reaction was complete. After 3 hours at −60° C., HBF$_4$ in diethyl ether was added (54%, 1.11 mL; 1.75 eq). The resulting suspension was stirred for 30 minutes. The precipitated tetrafluoroborate salt formed was isolated by filtration and dried under vacuum. 1.24 g (62%) of the desired product was obtained as a white solid. mp: 140-142° C.

¹H NMR (CDCl₃, 400 MHz): δ 7.87 (2H, d, J=7.5 Hz), 7.72-7.65 (4H, m), 5.64 (1H, d, J=10.2 Hz), 5.55 (1H, d, J=10.1 Hz), 2.51 (3H, s), 2.43 (3H, s), 2.29 (3H, s), 2.27 (3H, s). ¹³C NMR (CDCl₃, 100 MHz): δ 144.2, 139.08, 139.02, 137.0, 134.8, 131.5, 130.5, 126.9, 124.1, 117.8, 34.9, 20.8, 17.5, 16.9, 16.8. FT-IR (KBr): 3000, 2913, 2852, 2775, 1635, 1579, 1465, 1444, 1402, 1280, 1029 cm¹.

EXAMPLE 35

Preparation of 1-((bromomethyl)sulfinyl)-4-methylbenzene Starting from 1-methyl-4-(methylsulfinyl)benzene

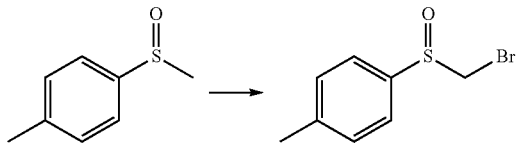

1-Methyl-4-(methylsulfinyl)benzene (0.814 g, 5.28 mmol) was dissolved in pyridine (0.939 mL, 2.2 eq) and acetonitrile (21 mL). The resulting solution was cooled to −40° C. A solution of bromine (1.7 g, 10.56 mmol) in acetonitrile (10 mL) was added slowly maintaining the same temperature. The reaction mixture was stirred at −40° C. for 1 h, and then overnight at r.t. The solvent was evaporated and the residue was dissolved in CH₂Cl₂ (10 mL) and aqueous solution of Na₂S₂O₃ (20%, 10 mL) at 0° C. was added. The mixture was extracted with CH₂Cl₂ (3×10 mL) and the combined organic phase was washed with HCl 10% (15 mL) and then with saturated NaHCO₃ (15 mL). The resulting organic phase was dried with anhydrous Na₂SO₄ and concentrated to afford 1.109 g of the desired product (90%) as white solid. mp: 46-47° C. ¹H NMR (CDCl₃, 300 MHz): δ 7.58 (2H, d, J=8.2 Hz), 7.36 (2H, d, J=7.9 Hz), 4.28 (2H, ABQ, J=10.0 Hz), 2.43 (3H, s). ¹³C NMR (CDCl₃, 100 MHz): δ 142.8, 138.3, 130.0, 124.8, 48.9, 21.5. FT-IR (KBr): 3027, 2939, 1594, 1492, 1353, 1176, 1105, 1041, 1016 cm⁻¹.

EXAMPLE 36

Preparation of (bromomethyl)(2,3,4,5-tetramethylphenyl)(p-tolyl)sulfonium tetrafluoroborate

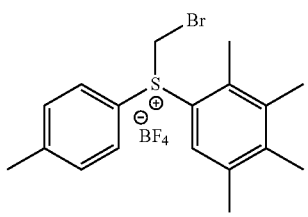

1-((Bromomethyl)sulfinyl)-4-methylbenzene (200 mg, 0.86 mmol) of example 35 was dissolved in dry diethyl ether (6 mL) under an argon atmosphere. 1,2,3,4-tetramethylbenzene (0.127 g, 1.1 eq) was added to the previous solution and then the mixture was cooled to a temperature below −60° C. After stabilizing the temperature, trifluoromethanesulfonic anhydride (0.145 mL, 1 eq) was slowly added maintaining the same temperature. After 30 minutes, HBF₄ in diethyl ether was added (54%, 0.209 mL, 1.5 eq). The resulting suspension was stirred for 30 minutes. The precipitate tetrafluoroborate salt was isolated by filtration and dried under vacuum. 0.309 g (82%) of the desired product was obtained as a white solid.

mp: 238° C. ¹H NMR (DMSO-d₆, 400 MHz): δ 7.98 (2H, d, J=8.4 Hz), 7.78 (1H, s), 7.58 (2H, d, J=8.2 Hz), 6.8 (2H, ABQ, J=9.08 Hz), 2.51 (3H, s), 2.42 (3H, s), 2.36 (3H, s), 2.26 (3H, s), 2.25 (3H, s). ¹³C NMR (DMSO-d₆, 100 MHz): δ 145.7, 142.8, 138.4, 137.3, 136.8, 131.6, 130.6, 126.2, 121.4, 120.5, 35.0, 20.9, 20.4, 17.1, 16.4. FT-IR (KBr): 3048, 2967, 1494, 1446, 1392, 1284, 1261, 1218, 1195, 1085, 1051, 1031, 862 cm⁻¹.

EXAMPLE 37

Preparation of (bromomethyl)(2,3,4,5-tetramethylphenyl)(p-tolyl)sulfonium triflate

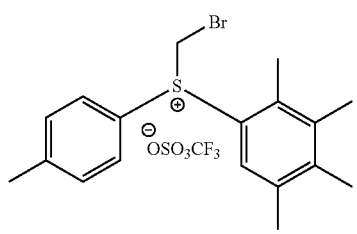

1-((bromomethyl)sulfinyl)-4-methylbenzene (200 mg, 0.86 mmol) of example 35 was dissolved in dry diethyl ether (6 mL) under argon atmosphere. 1,2,3,4-tetramethylbenzene (0.127 g, 1.1 eq) was added to the previous solution and then the mixture was cooled to a temperature below −60° C. After stabilizing the temperature below −60° C., trifluoromethanesulfonic anhydride (0.145 mL, 1 eq) was slowly added maintaining the same temperature. After 4 hours at −60° C., the precipitate triflate salt was isolated by filtration and dried under vacuum. 0.358 g (83%) of the desired product was obtained as a white solid. mp: 136-138° C. ¹H NMR (CDCl₃, 400 MHz): δ 7.81 (2H, d, J=8.4 Hz), 7.71 (1H, s), 7.46 (2H, d, J=8.2 Hz), 5.69 (2H, ABQ, J=10.0 Hz), 2.50 (3H, s), 2.43 (3H, s), 2.42 (3H, s), 2.27 (3H, s), 2.26 (3H, s). ¹³C NMR (CDCl₃, 100 MHz): δ 146.5, 143.9, 138.9, 138.8, 136.7, 132.2, 130.6, 126.9, 120.4, 118.5, 35.2, 21.6, 20.8, 17.4, 16.88, 16.81. FT-IR (KBr): 3027, 2954, 1492, 1450, 1400, 1288, 1245, 1220, 1162, 1147, 1027 cm⁻¹.

EXAMPLE 38

Preparation of loteprednol etabonate (chloromethyl 17-ethoxycarbonyloxy-11-hydroxy-10,13-dimethyl-3-oxo-7,8,9,11,12,14,15,16-octahydro-6H-cyclopenta[a]phenanthrene-17-carboxylate) Starting from 17-Ethoxycarbonyloxy-11-hydroxy-10,13-dimethyl-3-oxo-7,8,9,11,12,14,15,16-octahydro-6H-cyclopenta[a]phenanthrene-17-carboxylic acid Using (chloromethyl)(phenyl)(2,3,4,5-tetramethylphenyl)sulfonium triflate salt as Reagent

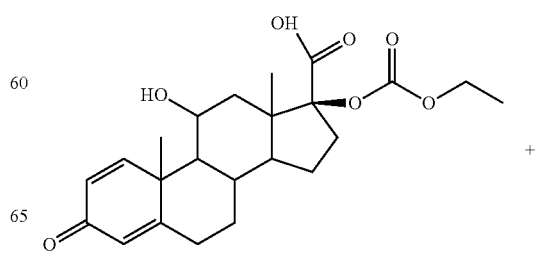

33

-continued

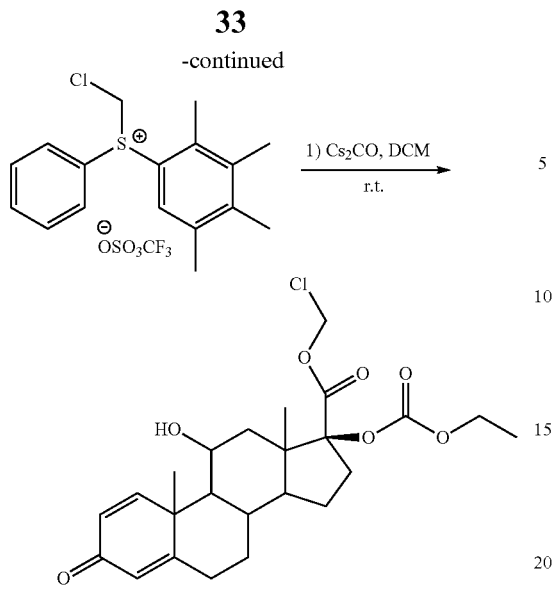

17-Ethoxycarbonyloxy-11-hydroxy-10,13-dimethyl-3-oxo-7,8,9,11,12,14,15,16-octahydro-6H-cyclopenta[a]phenanthrene-17-carboxylic acid (2 g, 4.78 mmol) of example 22 was suspended in acetonitrile (20 mL). Cesium carbonate (942.08 mg, 0.6 eq) was added. The resulting suspension was stirred for 75 minutes at 35° C. (Chloromethyl)(phenyl)(2,3,4,5-tetramethylphenyl)sulfonium triflate salt of example 22 (2.76 g, 1.27 eq) was added. The suspension was stirred at 35° C. until the reaction was complete. Water (50 mL) was added to the suspension and then the suspension was cooled to 0° C. The solid was isolated by filtration and dried under vacuum at a temperature below 35° C. (3.31 g). The solid was recrystallized from a mixture of acetone and water (1.86 g; 93% w/w). The salts are purged during this recrystallization.

EXAMPLE 39

Preparation of loteprednol etabonate (chloromethyl 17-ethoxycarbonyloxy-11-hydroxy-10,13-dimethyl-3-oxo-7,8,9,11,12,14,15,16-octahydro-6H-cyclopenta[a]phenanthrene-17-carboxylate) starting from 17-Ethoxycarbonyloxy-11-hydroxy-10,13-dimethyl-3-oxo-7,8,9,11,12,14,15,16-octahydro-6H-cyclopenta[a]phenanthrene-17-carboxylic acid Using (chloromethyl)(phenyl)(2,3,4,5-tetramethylphenyl)sulfonium tetrafluoroborate salt

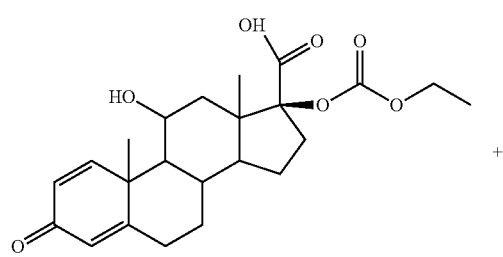

+

34

-continued

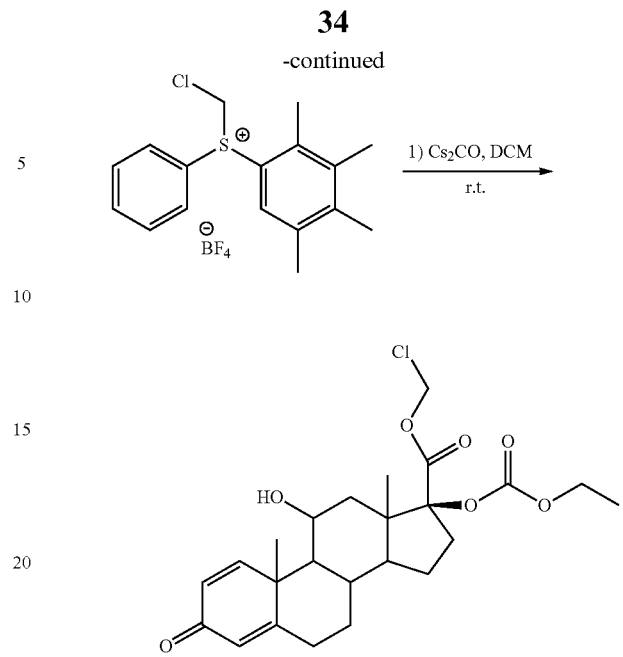

17-Ethoxycarbonyloxy-11-hydroxy-10,13-dimethyl-3-oxo-7,8,9,11,12,14,15,16-octahydro-6H-cyclopenta[a]phenanthrene-17-carboxylic acid (2 g, 4.78 mmol) was suspended in acetonitrile (20 mL). Cesium carbonate (942.08 mg, 0.6 eq) was added. The resulting suspension was stirred for 75 minutes at 35° C. (Chloromethyl)(phenyl)(2,3,4,5-tetramethylphenyl)sulfonium tetrafluoroborate of example 23 (2.73 g, 1.27 eq) was added. The suspension was stirred at 35° C. until the reaction was complete. Water (50 mL) was added to the suspension and then the suspension was cooled to 0° C. The solid was isolated by filtration and dried under vacuum at a temperature below 35° C. (3.70 g). The solid was recrystallized from a mixture of acetone and water (2.70 g; 135% w/w). The salts are purged during this recrystallization.

EXAMPLE 40

Preparation of (6S,9R,16R,17R)-17-(((chloromethyl)thio)carbonyl)-6,9-difluoro-11-hydroxy-10,13,16-trimethyl-3-oxo-6,7,8,9,10,11,12,13,14,15,16,17-dodecahydro-3H-cyclopenta[a]phenanthren-17-yl propionate Using (chloromethyl)(phenyl)(2,3,4,5-tetramethylphenyl)sulfonium triflate as Reagent

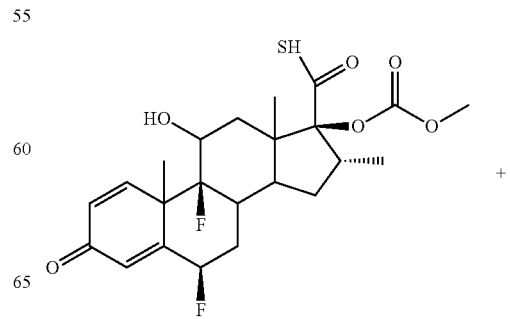

+

35

-continued

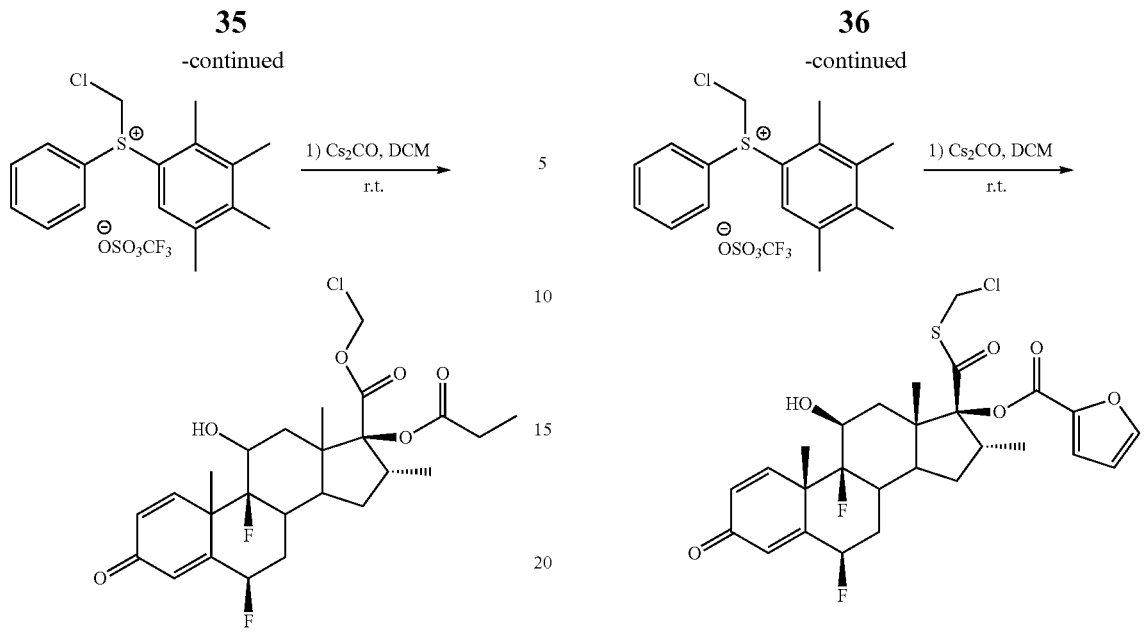

2.5 g (5.34 mmol) of 17-propionate carbothioic acid was dissolved in dichloromethane (25 mL). Cesium carbonate (1.74 g, 1.0 eq) was added and the resulting mixture was stirred for 30 minutes at room temperature. (chloromethyl)(phenyl)(2,3,4,5-tetramethylphenyl)sulfonium triflate of example 22 (3.53 g, 1.5 eq) was added. The reaction mixture was stirred at room temperature until the reaction is complete. The mixture was added to heptane (100 mL). The resulting suspension was stirred for 30 minutes. The solid was isolated by filtration, washed with heptane (10 mL) and dried under vacuum at a temperature below 35° C. The product was recrystallized from a mixture of acetone and water. The salts are purged during this recrystallization. 2.30 g of product was obtained as white solid.

EXAMPLE 41

Preparation of (6S,9R,10S,11S,13S,16R,17R)-17-(((chloromethyl)thio)carbonyl)-6,9-difluoro-11-hydroxy-10,13,16-trimethyl-3-oxo-6,7,8,9,10,11,12,13,14,15,16,17-dodecahydro-3H-cyclopenta[a]phenanthren-17-yl furan-2-carboxylate Using (chloromethyl)(phenyl)(2,3,4,5-tetramethylphenyl)sulfonium triflate as Reagent

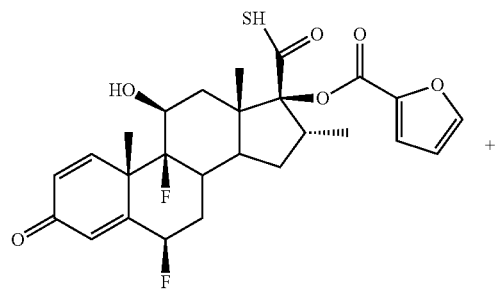

+

36

-continued 2.5 g (4.95 mmol) of Carbothioic acid 17-furoate was suspended in dichloromethane (25 mL). Cesium carbonate (1.61 g, 1.0 eq) was added and the resulting mixture was stirred for 30 minutes at room temperature. (chloromethyl)(phenyl)(2,3,4,5-tetramethylphenyl)sulfonium triflate of example 22 (3.26 g, 1.5 eq) was added. The reaction mixture was stirred at room temperature until the reaction is complete. The mixture was added to heptane (100 mL). The resulting suspension was stirred for 30 minutes. The solid was isolated by filtration, washed with heptane (10 mL) and dried under vacuum at a temperature below 35° C. The product was recrystallized from a mixture of methanol and water. The salts are purged during this recrystallization. 2.20 g of product was obtained as white solid.

It is evident to one skilled in the art that this invention is not limited to the forgoing examples, and that can be embodied in other specific forms without departing from the spirit and scope thereof. Thus, the examples should be considered as illustrative and not restrictive, reference being made to the claims, and that all changes which come within the meaning and range of equivalency of claims be embraced therein.

The invention claimed is:

1. A compound of formula A

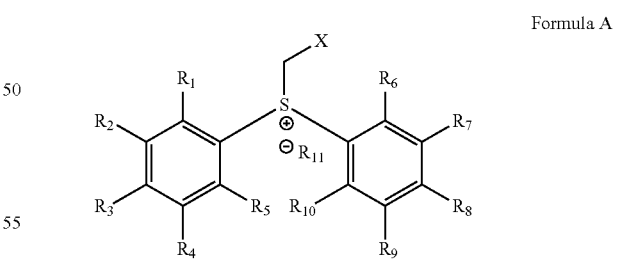

Formula A wherein X represents F; $R_1$-$R_5$, $R_6$, $R_9$ and $R_{10}$ represent H; $R_7$ and $R_8$ represent alkyl; and $R_{11}$ represents tetrafluoroborate.

2. The compound of claim 1, wherein $R_7$ and $R_8$ represent methyl.

* * * * *